(12) United States Patent
Aoki et al.

(10) Patent No.: US 10,441,731 B2
(45) Date of Patent: Oct. 15, 2019

(54) PHARMACEUTICAL INJECTION DEVICE, AND METHOD FOR CONTROLLING PHARMACEUTICAL INJECTION DEVICE

(71) Applicant: PHC Holdings Corporation, Minato-ku, Tokyo (JP)

(72) Inventors: Tooru Aoki, Ehime (JP); Kenji Murakami, Ehime (JP); Takahiko Tanida, Ehime (JP); Hiroshi Suzuki, Ehime (JP); Shinsuke Hata, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 267 days.

(21) Appl. No.: 15/037,321

(22) PCT Filed: Nov. 25, 2014

(86) PCT No.: PCT/JP2014/081096
§ 371 (c)(1),
(2) Date: May 17, 2016

(87) PCT Pub. No.: WO2015/098399
PCT Pub. Date: Jul. 2, 2015

(65) Prior Publication Data
US 2016/0287815 A1    Oct. 6, 2016

(30) Foreign Application Priority Data

Dec. 27, 2013 (JP) .................. 2013-273255

(51) Int. Cl.
*A61M 5/50* (2006.01)
*A61M 5/24* (2006.01)
(Continued)

(52) U.S. Cl.
CPC ............ *A61M 5/5086* (2013.01); *A61M 5/20* (2013.01); *A61M 5/24* (2013.01);
(Continued)

(58) Field of Classification Search
CPC ........ A61M 5/5086; A61M 5/20; A61M 5/24; A61M 2205/502; A61M 2205/18;
(Continued)

(56) References Cited

U.S. PATENT DOCUMENTS 4,776,702 A   10/1988   Yamaba
6,585,698 B1   7/2003   Packman et al.
(Continued)

FOREIGN PATENT DOCUMENTS

JP   S62-223634 A   10/1987
JP   H08-068788 A    3/1996
(Continued)

OTHER PUBLICATIONS

Decision to Grant from the corresponding Japanese Patent Application No. 2015-554685 dated Mar. 14, 2017.
(Continued)

*Primary Examiner* — Jenna Zhang
(74) *Attorney, Agent, or Firm* — Wenderoth, Lind & Ponack, L.L.P.

(57) ABSTRACT

A pharmaceutical injection device may comprise a main body case having a cartridge holder, a piston that pushes out the pharmaceutical of a pharmaceutical cartridge held in the cartridge holder, a light emitting component, a light receiving component, and a controller. The light emitting component may shine light of different colors on the pharmaceutical cartridge disposed in the cartridge holder. The light receiving component receives light that has been shined from the light emitting component onto the pharmaceutical cartridge and reflected by the pharmaceutical cartridge. The controller may shine from the light emitting component and identify the type of pharmaceutical cartridge.

7 Claims, 23 Drawing Sheets

(51) Int. Cl.
*A61M 5/20* (2006.01)
*A61M 5/315* (2006.01)

(52) U.S. Cl.
CPC .............. *A61M 2005/2481* (2013.01); *A61M 2005/2496* (2013.01); *A61M 2005/31588* (2013.01); *A61M 2205/14* (2013.01); *A61M 2205/18* (2013.01); *A61M 2205/3306* (2013.01); *A61M 2205/502* (2013.01); *A61M 2205/52* (2013.01); *A61M 2205/584* (2013.01); *A61M 2205/6063* (2013.01); *A61M 2205/6081* (2013.01)

(58) Field of Classification Search
CPC ........ A61M 2205/584; A61M 2205/52; A61M 2205/3306; A61M 2205/6081; A61M 2205/14; A61M 2205/6063; A61M 2005/2481; A61M 2005/31588; A61M 2005/2496
See application file for complete search history.

(56) References Cited

U.S. PATENT DOCUMENTS

| | | | | |
|---|---|---|---|---|
| 8,827,964 B2* | 9/2014 | Boyd | ...................... | A61M 5/24 604/189 |
| 8,882,964 B2* | 11/2014 | Zhao | .................... | D21H 17/375 162/147 |
| 9,498,300 B1* | 11/2016 | Sanchez, Jr. | ............ | A61B 90/92 |
| 2005/0171476 A1 | 8/2005 | Judson et al. | | |
| 2006/0224123 A1 | 10/2006 | Friedli et al. | | |
| 2010/0168711 A1* | 7/2010 | Bazargan | ........... | A61B 5/14532 604/404 |
| 2011/0238017 A1* | 9/2011 | Watanabe | ......... | A61M 5/14546 604/189 |
| 2012/0209111 A1* | 8/2012 | Cowan | .................. | A61M 5/007 600/432 |
| 2013/0072897 A1 | 3/2013 | Day et al. | | |
| 2013/0221097 A1 | 8/2013 | Day et al. | | |
| 2013/0253472 A1 | 9/2013 | Cabiri | | |
| 2014/0228805 A1 | 8/2014 | Mudd et al. | | |
| 2014/0243750 A1* | 8/2014 | Larsen | ................ | A61M 5/1452 604/189 |
| 2014/0330215 A1* | 11/2014 | Kikuchi | .................. | A61M 5/20 604/189 |
| 2016/0074593 A1* | 3/2016 | Heumann | ............... | A61M 5/28 604/189 |

FOREIGN PATENT DOCUMENTS

| | | |
|---|---|---|
| JP | H08-110297 A | 4/1996 |
| JP | 2000-513967 A | 10/2000 |
| JP | 2001-170176 A | 6/2001 |
| JP | 2007-506470 A | 3/2007 |
| JP | 2013-039394 A | 2/2013 |
| JP | 2013-534163 A | 9/2013 |
| WO | 1998/000187 A1 | 1/1998 |
| WO | 2010/070799 A1 | 6/2010 |
| WO | 2010/078084 A2 | 7/2010 |
| WO | 2011/089205 A2 | 7/2011 |
| WO | 2013/050535 A2 | 4/2013 |
| WO | 2013/074364 A1 | 5/2013 |

OTHER PUBLICATIONS

European Search Report from the corresponding European Patent Application No. 14873828.9 dated Jan. 18, 2017.
The Search Report from the corresponding International Patent Application No. PCT/JP2014/081096 dated Mar. 10, 2015.

* cited by examiner

FIG. 16

TABLE(0)

| Condition | Pharmaceutical | Value calculated from measured value | | | | Color of color label | | |
|---|---|---|---|---|---|---|---|---|
| | | PRG | PRB | PGB | PB' | R | G | B |
| | 0 | 0 | 0 | – | – | 252 | 0 | 0 |
| | 1 | 0 | 0.5 | – | – | 252 | 0 | 126 |
| | 2 | 0 | 1 | – | – | 252 | 0 | 252 |
| | 3 | 0 | 2 | – | – | 126 | 0 | 252 |
| | 4 | 0.5 | 0 | – | – | 252 | 126 | 0 |
| | 5 | 0.5 | 0.5 | – | – | 252 | 126 | 126 |
| PR'≧Pm | 6 | 0.5 | 1 | – | – | 252 | 126 | 252 |
| | 7 | 1 | 0 | – | – | 252 | 252 | 0 |
| | 8 | 1 | 0.5 | – | – | 252 | 252 | 126 |
| | 9 | 1 | 1 | – | – | 252 | 252 | 252 |
| | 10 | 2 | 0 | – | – | 126 | 252 | 0 |
| | 11 | 2 | 1 | – | – | 126 | 252 | 126 |
| | 12 | 2 | 1 | – | – | 126 | 252 | 126 |
| | 13 | 2 | 2 | – | – | 126 | 252 | 252 |

TABLE(1)

| Condition | Pharmaceutical | Value calculated from measured value ||||  Color of color label |||
|---|---|---|---|---|---|---|---|---|
| | | PRG | PRB | PGB | PB' | R | G | B |
| PR'<Pm<br>PG'≧Pm | 14 | – | – | 0 | – | 0 | 252 | 0 |
| | 15 | – | – | 0.5 | – | 0 | 252 | 126 |
| | 16 | – | – | 1 | – | 0 | 252 | 252 |
| | 17 | – | – | 2 | – | 0 | 126 | 252 |

FIG. 17

TABLE(2)

| Condition | Pharmaceutical | Value calculated from measured value | | | | Color of color label | | |
|---|---|---|---|---|---|---|---|---|
| | | PRG | PRB | PGB | PB' | R | G | B |
| PR'<Pm<br>PG'<Pm<br>PB'≧Pm | 18 | — | — | — | 252 | 0 | 0 | 252 |

FIG. 18

PHARMACEUTICAL INJECTION DEVICE, AND METHOD FOR CONTROLLING PHARMACEUTICAL INJECTION DEVICE

PRIORITY

This is a National Stage Application under 35 U.S.C. § 365 of International Application PCT/JP2014/081096, with an international filing date of Nov. 25, 2014, which claims priority to Japanese Patent Application No. 2013-273255 filed on Dec. 27, 2013. The entire disclosures of International Application PCT/JP2014/081096 and Japanese Patent Application No. 2013-273255 are hereby incorporated herein by reference.

TECHNICAL FIELD

Certain implementations relate to a pharmaceutical injection device for injecting a pharmaceutical, such as insulin or a growth hormone, as well as to a method for controlling a pharmaceutical injection device.

BACKGROUND

A conventional pharmaceutical injection device of this type was configured to comprise a main body case having a pharmaceutical cartridge holder, a piston that pushed the pharmaceutical of the pharmaceutical cartridge housed in the holder inside the main body case to the outside of the pharmaceutical cartridge, and a controller that was connected to this piston.

The configuration was also such that the controller was connected to a light emitting element that shined white light onto the pharmaceutical cartridge disposed in the holder, and a color sensor that received light that was shined from the light emitting element onto the pharmaceutical cartridge and reflected by this pharmaceutical cartridge.

A color label for identifying the type of pharmaceutical cartridge was attached to this cartridge. When white light was shined onto this color label, the color of the color label was reflected, this reflected light was received by a light receiving element, and the color label was sensed by the color sensor.

Therefore, the controller was able to identify the type of pharmaceutical cartridge from the color sensed by the color sensor.

SUMMARY

However, a problem encountered with the above-mentioned conventional pharmaceutical injection device was that soiling of the color sensor would sometimes prevent the proper identification of the type of pharmaceutical cartridge.

Actually, a transparent cover is usually provided to the front side of the color sensor, and soiling of this transparent cover can make it impossible to properly identify the type of pharmaceutical cartridge.

Specifically, since the pharmaceutical cartridge is housed in the holder, if dust or dirt should get into the holder as the cartridge is being put in, for example, and this dust or dirt should adhere to the transparent cover, then the color sensor will no longer be able to perform its function.

More specifically, as is well know, with a color sensor serving as a reflected light sensor, numerous RGB sensors or the like are disposed, but if some of those sensors should be covered with dust or dirt, they will no longer be able to sense the corresponding R, G, or B components.

The controller senses the color of the color label affixed to the pharmaceutical cartridge based on the sensed amount of the R, G, and B components, so in a state in which some of the R, G, or B components cannot be sensed as mentioned above, the color may end up being incorrectly identified, and it may be impossible to properly identify the type of pharmaceutical cartridge.

In view of this, it is preferred to be able to properly identify the type of pharmaceutical cartridge.

To achieve the stated object, the pharmaceutical injection device may comprise a main body case having a pharmaceutical cartridge holder, a piston that pushes the pharmaceutical of the pharmaceutical cartridge housed in the holder inside the main body case to the outside of the pharmaceutical cartridge, a light emitting component that shines light of different colors on the pharmaceutical cartridge disposed in the holder, a light receiving component that receives light shined from the light emitting component onto the pharmaceutical cartridge and reflected by the pharmaceutical cartridge, and a controller that successively shines light of different colors from the light emitting component onto the pharmaceutical cartridge, and identifies the type of pharmaceutical cartridge on the basis of the amount of light received by the light receiving component for each color. The controller issues a warning output if the amount of light of the sensed color exhibiting the greatest amount of light out of the light quantities for the various colors received by the light receiving component is lower than a specific value.

Specifically, the pharmaceutical injection device may comprise a light emitting component that shines light of different colors onto the pharmaceutical cartridge disposed in the holder, and a light receiving component that receives light shined from the light emitting component onto the pharmaceutical cartridge and reflected by the pharmaceutical cartridge.

Also, the controller successively shines light of different colors from the light emitting component onto the pharmaceutical cartridge, and identifies the type of pharmaceutical cartridge on the basis of the amount of light received by the light receiving component for each color.

Accordingly, even if dirt or dust should adhere to the light receiving component, when light of different colors is shined from the light emitting component onto the pharmaceutical cartridge, the amount of light received by the light receiving component for each color will just decrease as the overall sensed level, and in this state, the controller will still be able to properly identify the type of pharmaceutical cartridge from the amount of light of each color.

With the pharmaceutical injection device and the method for controlling a pharmaceutical injection device, the type of pharmaceutical cartridge can be properly identified.

BRIEF DESCRIPTION OF THE DRAWINGS

FIG. 16 is a table of reference data for the memory of the pharmaceutical injection device pertaining to an embodiment of the present invention;

FIG. 17 is a table of reference data for the memory of the pharmaceutical injection device pertaining to an embodiment of the present invention;

FIG. 18 is a table of reference data for the memory of the pharmaceutical injection device pertaining to an embodiment of the present invention;

DETAILED DESCRIPTION

Implementations will now be described through reference to the drawings.

Embodiment 1

External Configuration of Pharmaceutical Injection Device

Figure 1:
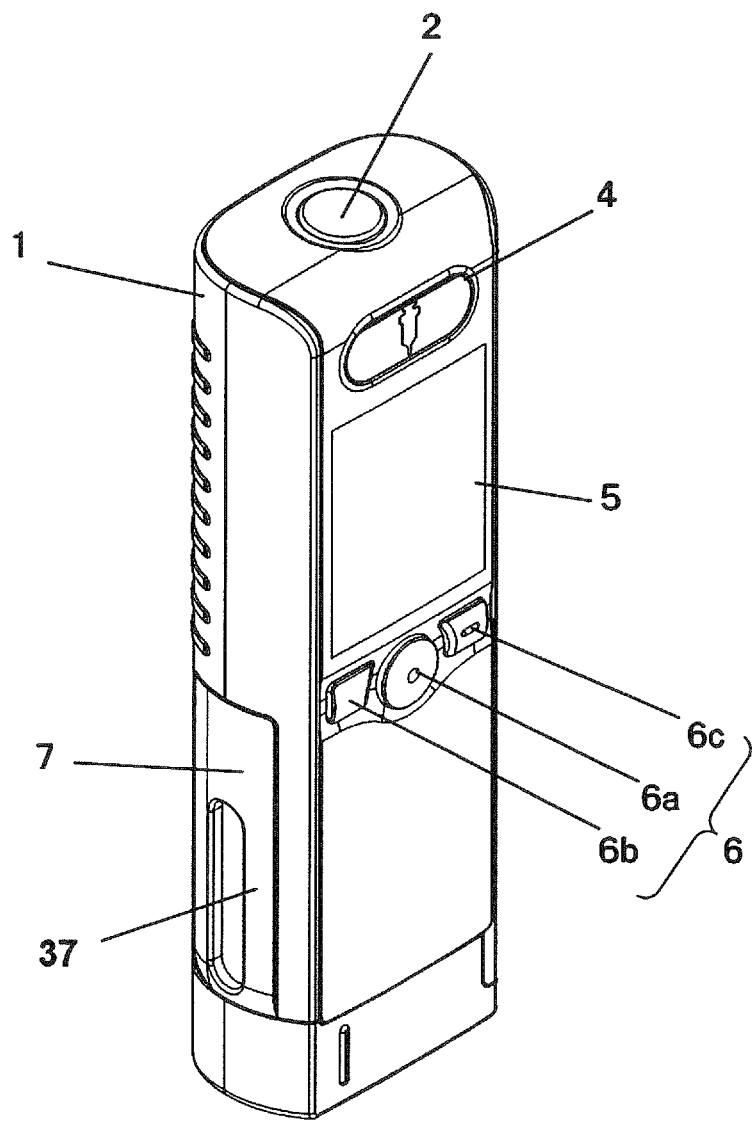
FIG. 1 is an oblique view of the pharmaceutical injection device pertaining to an embodiment of the present invention.
Figure 2:
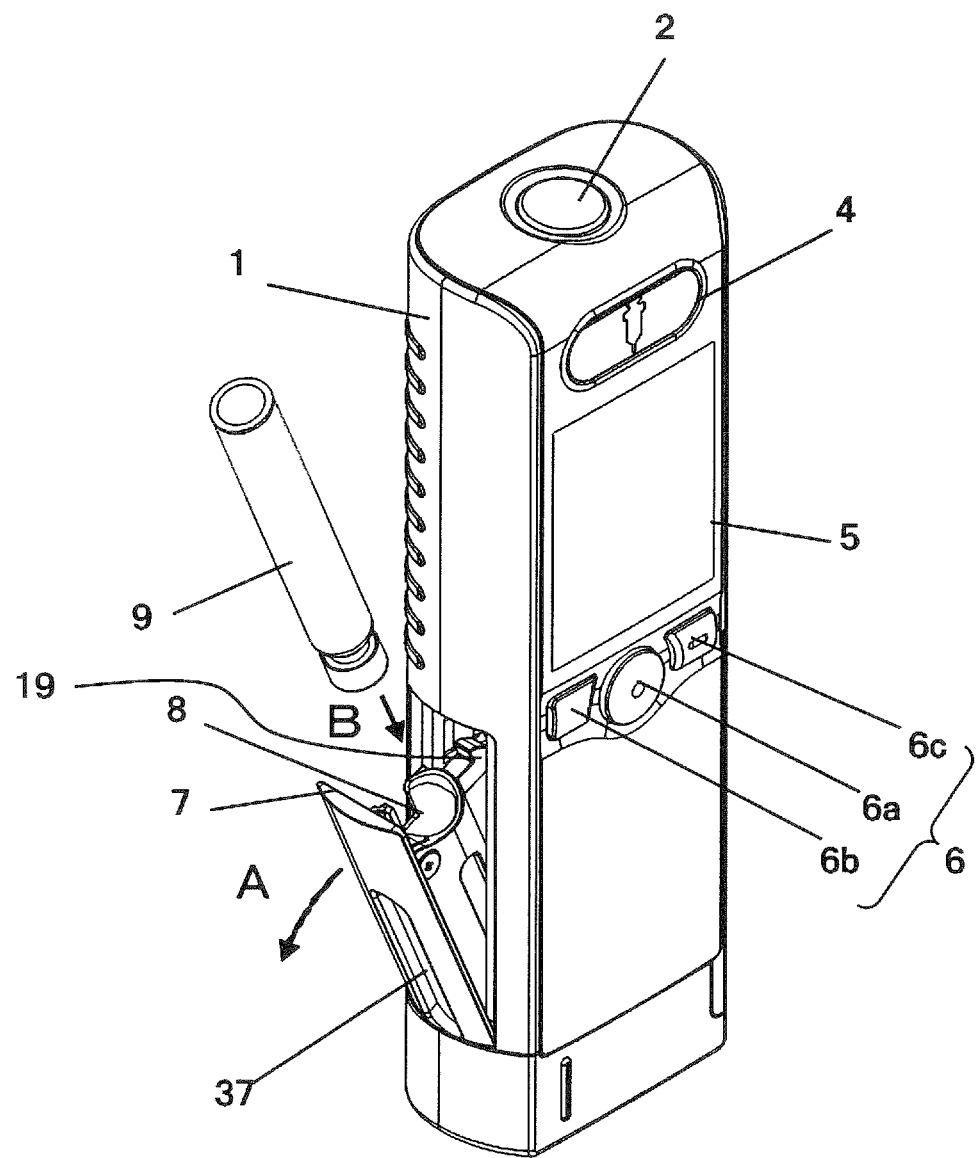
FIG. 2 is an oblique view of the pharmaceutical injection device pertaining to an embodiment of the present invention when the cartridge holder has been opened.
Figure 3:
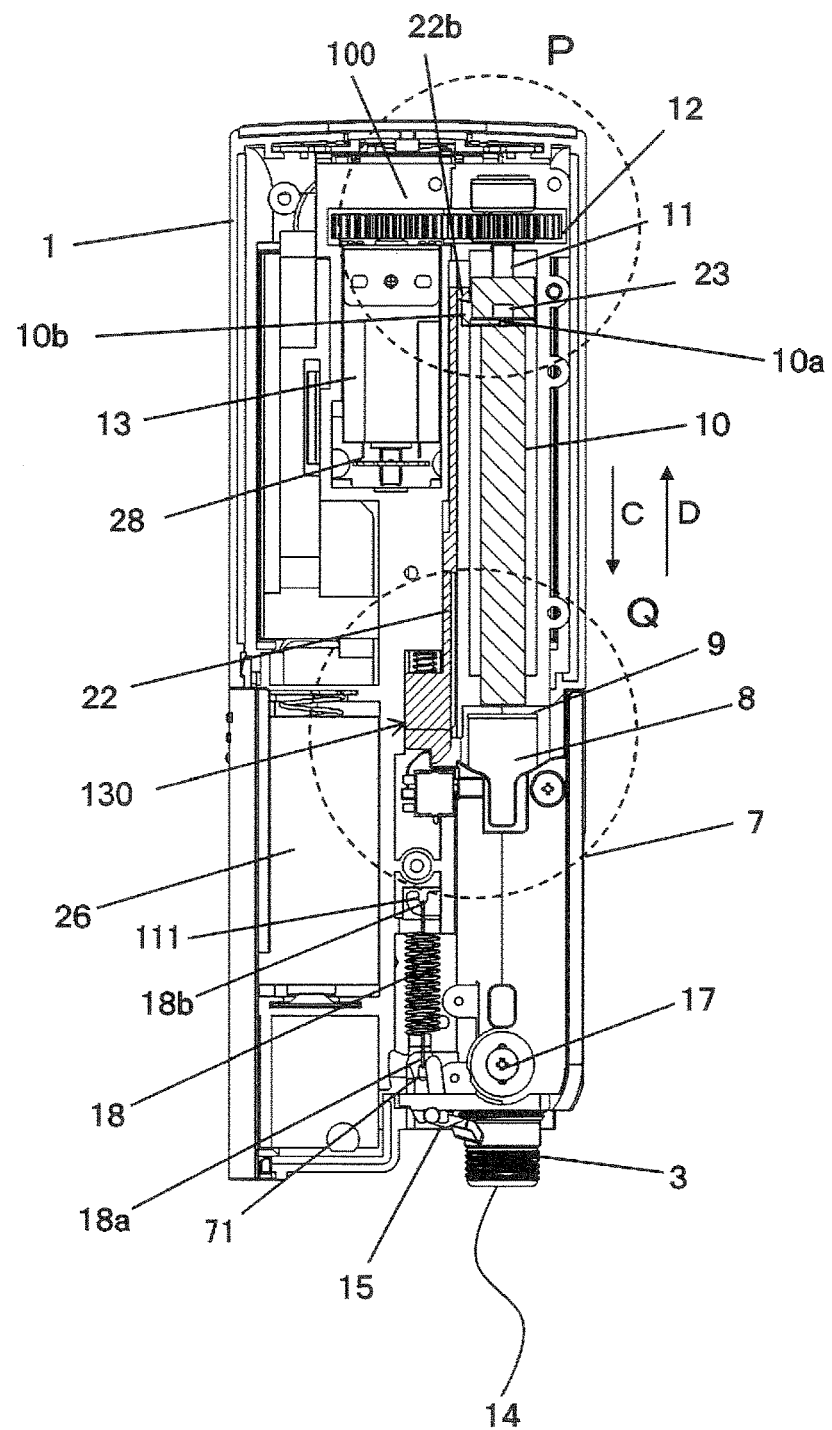
FIG. 3 is a front cross section of the internal configuration of the pharmaceutical injection device pertaining to an embodiment of the present invention.

FIG. 1 is an oblique view of the pharmaceutical injection device in this embodiment. FIG. 2 is an oblique view of the pharmaceutical injection device in this embodiment when the cartridge holder has been opened. FIG. 3 is a front cross section of the internal configuration of the pharmaceutical injection device in this embodiment.

As shown in FIGS. 1 and 2, the pharmaceutical injection device in this embodiment comprises a cylindrical main body case 1. A power switch 2 is provided to the upper face of this main body case 1, and an injection needle mounting component 3 is provided to the lower face as shown in FIG. 3. In this Specification, for the sake of convenience the side on which the power switch 2 is provided will be called the top or rear, and the opposite side on which the injection needle mounting component 3 is provided will be called the bottom or front.

A pharmaceutical injection switch 4, a display component 5, and setting switches 6 for setting the pharmaceutical dose are provided in that order from top to bottom on the front portion of this main body case 1. The setting switches 6 consist of a setting switch 6a in the middle, a setting switch 6b on the left side, and a setting switch 6c on the right side.

As shown in FIGS. 1 and 2, a cylindrical cartridge holder 7 (an example of the holder of a pharmaceutical cartridge 9) is provided to the main body case 1 so that it can be opened and closed.

That is, the cartridge holder 7 is first opened up as indicated by the arrow A in FIG. 2, then the pharmaceutical cartridge 9 is inserted as indicated by the arrow B through an insertion opening 8 provided in the top face of the cartridge holder 7, after which the cartridge holder 7 is closed as shown in FIG. 1, so that the pharmaceutical cartridge 9 is installed in the main body case 1 as shown in FIG. 3.

Internal Configuration of Pharmaceutical Injection Device

FIG. 4a is a diagram of the configuration near the insertion opening 8 of the cartridge holder 7, and is a detail view of the Q portion in FIG. 3. FIG. 4b is a diagram of the configuration of a home sensor 23, and is a detail view of the P portion in FIG. 3. FIGS. 3, 4a, and 4b show the state when a piston 10 is disposed at the origin position (discussed below).

As shown in FIGS. 3 and 4b, the piston 10 is provided above the insertion opening 8 of the cartridge holder 7 in the main body case 1. This piston 10 is inserted into or pulled out of the pharmaceutical cartridge 9 through the insertion opening 8 of the cartridge holder 7 by a piston drive mechanism 100 having a feed screw 11, a gear 12, and a motor 13. In FIG. 3, the insertion direction in which the piston 10 is inserted into the pharmaceutical cartridge 9 mounted to the cartridge holder 7 (also referred to as the downward or forward direction) is indicated by the arrow C, while the pull-out direction in which the piston 10 is pulled out of the pharmaceutical cartridge 9 mounted to the cartridge holder 7 (also referred to as the upward or rearward direction) is indicated by the arrow D.

Configuration of Cartridge Holder 7 and Nearby Area

The cartridge holder 7 will now be described in detail through reference to FIGS. 1 to 4.

As discussed above, the cartridge holder 7 is cylindrical in shape, having the insertion opening 8 in its top face, and as shown in FIG. 3, an opening 14 is also provided to the bottom face, threads are formed around the outer peripheral part of this opening 14, and this threaded part becomes the injection needle mounting component 3.

Figure 5:
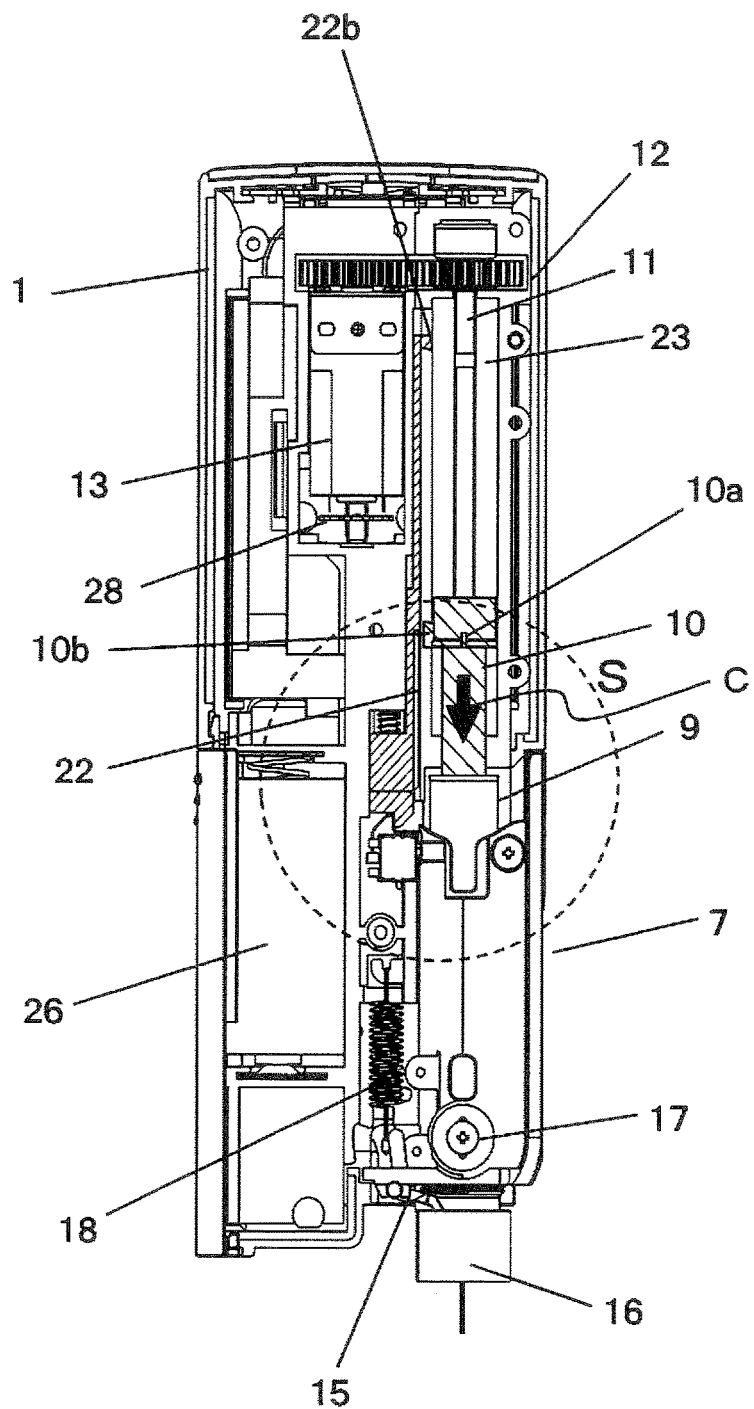
FIG. 5 is a front cross section of the internal configuration of the pharmaceutical injection device pertaining to an embodiment of the present invention.

A needle detector switch 15 is also provided to this injection needle mounting component 3. As shown in FIG. 5 (discussed below), this needle detector switch 15 detects whether or not an injection needle 16 has been attached to the injection needle mounting component 3.

An axial support 17 for supporting the cartridge holder 7 so that it can be opened and closed with respect to the main body case 1 is provided to the lower outer peripheral face of the cartridge holder 7.

The opposite side (inner side) of this axial support 17 from the open side of the cartridge holder 7 is linked to one end of an ejector spring 18, which is used as an example of a biasing member. The other end of the ejector spring 18 is linked to the main body case 1 above.

Specifically, as shown in FIG. 3, a holder-side linking component 71 that links to the first end 18a of the ejector spring 18 is formed on the inner portion of the end on the opening 14 side of the cartridge holder 7. The ejector spring 18 is disposed along the cartridge holder 7 to the inside of the cartridge holder 7 in a state in which the cartridge holder 7 is closed, and the second end 18b of the ejector spring 18 is linked to a main body-side linking component 111 formed on the main body case 1, on the insertion opening 8 side.

That is, the cartridge holder 7 is such that when a force is applied in the direction in which the ejector spring 18 contracts, the insertion opening 8 portion above is biased in the direction of opening with respect to the main body case 1, as shown in FIG. 2.

Also, a latched component 19 is provided as shown in FIG. 4a to the upper part of the cartridge holder 7 so that the cartridge holder 7 will be held in its closed position as shown in FIGS. 1 and 3 against the opening-direction biasing by the ejector spring 18.

Furthermore, an ejector pawl 20 that latches the latched component 19 is provided above the latched component 19 in the main body case 1. This ejector pawl 20 is adjacent to the lower end side of a protrusion 22a on the lower end side of a slender lever 22, and is linked to the protrusion 22a. A spring 21 is in contact with the opposite side of the protrusion 22a from the ejector pawl 20, and the protrusion 22a and the ejector pawl 20 are biased in the downward latched component 19 direction (the insertion direction C) (see FIG. 4a).

The ejector pawl 20 also has on its inside a contact face 20a formed parallel to the movement direction of the piston 10. When the cartridge holder 7 has been closed, a contact face 19a formed parallel to the movement direction of the piston 10 is disposed on the outside of the latched component 19. Thus, the contact face 20a and the contact face 19a come into contact with each other, and this holds the cartridge holder 7 closed.

The ejector pawl 20 also has a sloped part 20b that slopes outward from the lower end of the contact face 20a. The latched component 19 has a sloped part 19b that slopes inward from the upper end of the contact face 19a. In the closing of the cartridge holder 7, the sloped part 20b slides upward with respect to the sloped part 19b, which affords smooth closure.

As shown in FIG. 4b, the lever 22 to which the ejector pawl 20 is linked has a protrusion 22b disposed diagonally across from the protrusion 22a (so that the protrusion direction is reversed). The protrusion 22b is provided on the feed screw 11 side of the piston 10 of the lever 22.

Specifically, as shown in FIG. 3, the slender lever 22 is disposed along the movement direction of the piston 10, aligned on the inner side of the piston 10 when it has not been inserted into the pharmaceutical cartridge 9. The protrusion 22a and the ejector pawl 20 are provided on the cartridge holder 7 side of the lever 22, and the protrusion 22b is provided on the gear 12 side of the lever 22. Thus, the lever 22 links the protrusion 22b and the ejector pawl 20, and the lever 22, the protrusion 22b, and the ejector pawl 20 are biased downward so as to latch the latched component 19 by the spring 21.

Configuration of Origin Sensor 23 and Nearby Area

As shown in FIG. 4b, the origin sensor 23, which senses the origin position of the piston 10, is provided on the rear end side of the piston 10 (the upper end side in FIG. 1). This origin sensor 23 is fixed on the inside of the main body case 1. A transmission type of photoelectronic sensor can be used, for example, as the origin sensor 23, and the origin position of the piston 10 is sensed when a protrusion 10a provided to the piston 10 blocks the light.

A protrusion 10b that protrudes to the lever 22 side is also provided to the piston 10. The protrusion 10b provided on the rear end part of the piston 10 and on lower than the protrusion 22b of the lever 22 (on the insertion direction C side). The protrusion 10b hits the protrusion 22b and retracts the entire lever 22 (moving upward in FIGS. 1 and 2) only when the piston 10 retracts upward beyond the origin position (when moving in the pull-out direction D).

On the other hand, during pharmaceutical injection (the state in FIGS. 5 and 6), if the piston 10 moves downward (that is, moves lower than the origin position), the protrusion 22b on the upper end side of the lever 22 moves downward along with the protrusion 10b provided to the rear end part of the piston 10. However, since the lever 22 has a structure that the lever 22 stops at the position shown in FIG. 3 (the lower end position) and is not allowed to descend any farther, if the piston 10 descends farther, the protrusion 22b on the upper end side of the lever 22 separates from the protrusion 10b of the piston 10. This structure that prevents descent can be realized by a configuration in which the lever 22, the protrusion 22b, and the ejector pawl 20 hit a protrusion (not shown) and stop upon reaching the position shown in FIG. 3. The position at which the ejector pawl 20 will not descend any farther is the dotted line position shown in FIG. 8 (discussed below).

Thus, the structure is such that the latched component 19 provided in the main body case 1 engages with the ejector pawl 20 adjacent to the protrusion 22a on the lower end side of the lever 22, and the cartridge holder 7 is held closed.

Specifically, the ejector pawl 20 attached to the protrusion 22a on the lower end side of the lever 22 returns to the origin position once the piston 10 has finished injecting all of the pharmaceutical in the pharmaceutical cartridge, and after the ejector pawl 20 has moved further upward, the ejector pawl 20 is disengaged from the latch component 19, and the cartridge holder 7 opens up.

In the above example, the ejector pawl 20 and the lever 22 are separate members that are linked, but this is not the only option, and they may instead be formed integrally.

Operation During Pharmaceutical Injection

Figure 6:
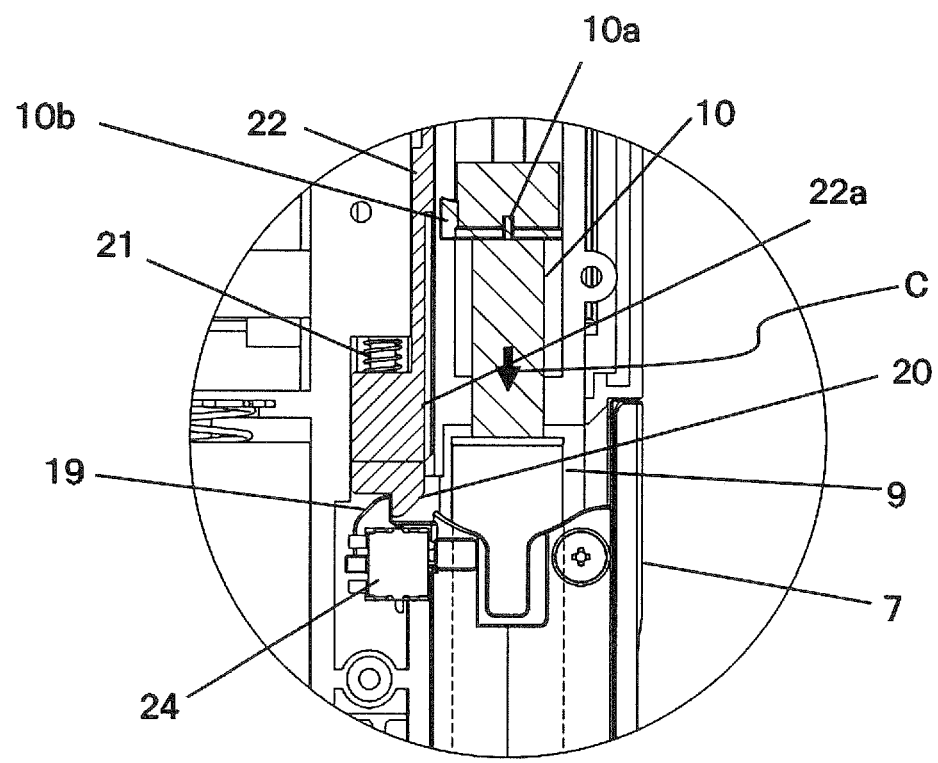
FIG. 6 is a detail view of the main components of the pharmaceutical injection device pertaining to an embodiment of the present invention.

FIG. 5 is a configuration diagram of the state of the pharmaceutical injection device in this embodiment during pharmaceutical injection. FIG. 6 is a detail view of the S portion in FIG. 5.

Figure 4:
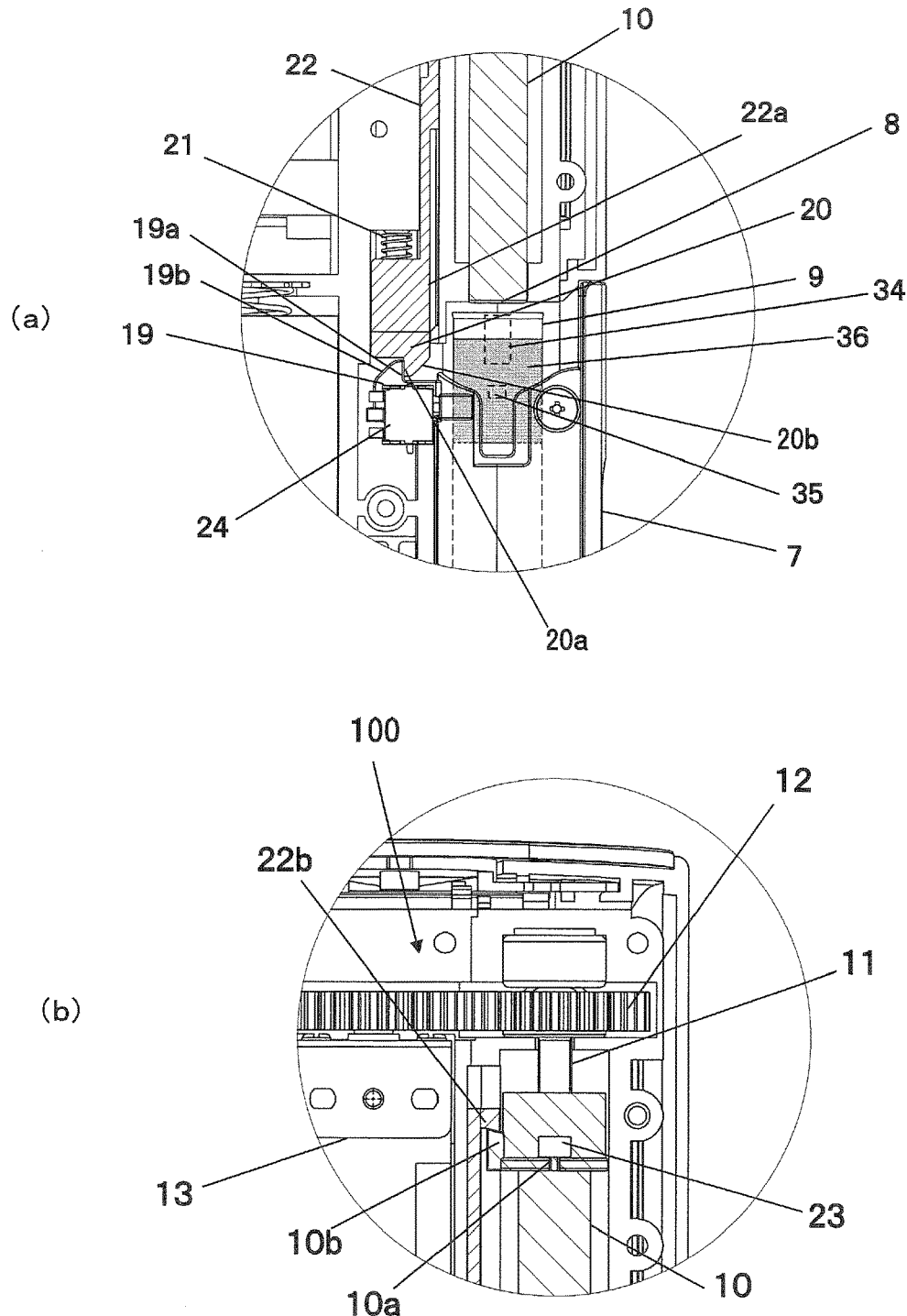
FIGS. 4a and 4b are detail views of the main components of the pharmaceutical injection device pertaining to an embodiment of the present invention.

FIGS. 3 and 4 show the initial state of the pharmaceutical injection device of an implementation (when the piston 10 is in its origin position), but FIGS. 5 and 6 show the operation of injecting the pharmaceutical (at the start of the injection operation).

Specifically, the injection of the pharmaceutical in the pharmaceutical cartridge 9 is started by pressing an inject button (see FIG. 2) provided on the outer peripheral surface of the main body case 1.

More specifically, the motor 13 (a part of the piston drive mechanism 100) is actuated, the gear 12 linked to the motor 13 rotates, and the rotation of the gear 12 rotates the feed screw 11. The piston drive mechanism 100 thus converts the rotational motion of the motor 13 into linear motion of the piston 10.

When the piston 10 moves downward, the distal end of the piston 10 hits a gasket 41 (see FIG. 12; discussed below) at the rear end of the pharmaceutical cartridge 9 (see FIG. 6). After this, when the piston 10 is moved again, the liquid pharmaceutical in the pharmaceutical cartridge 9 is injected under the skin through the injection needle 16 attached to the distal end part of the pharmaceutical cartridge 9.

Operation During Ejection of Cartridge Holder 7

Figure 7:
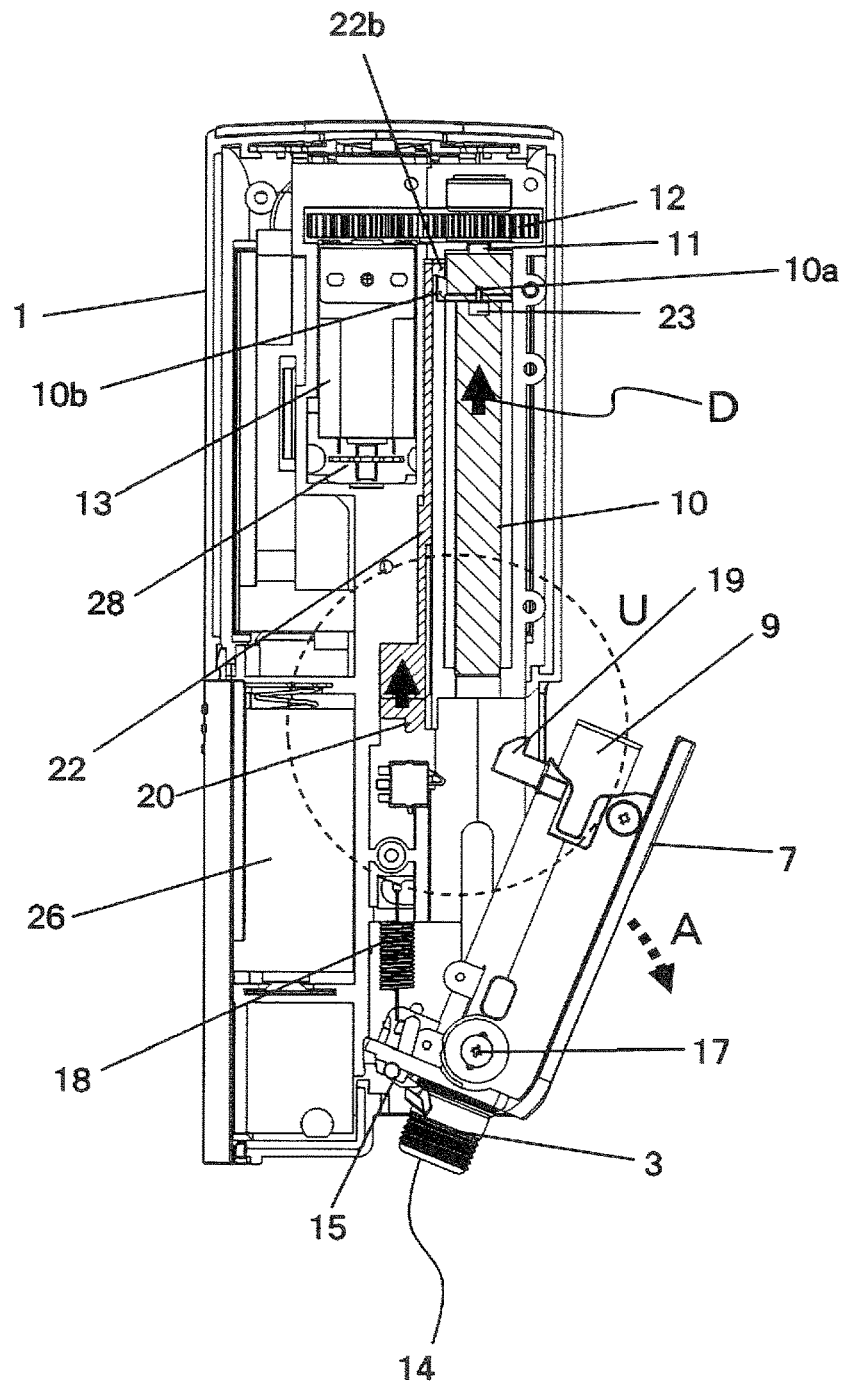
FIG. 7 is a front cross section of the internal configuration of the pharmaceutical injection device pertaining to an embodiment of the present invention.
Figure 8:
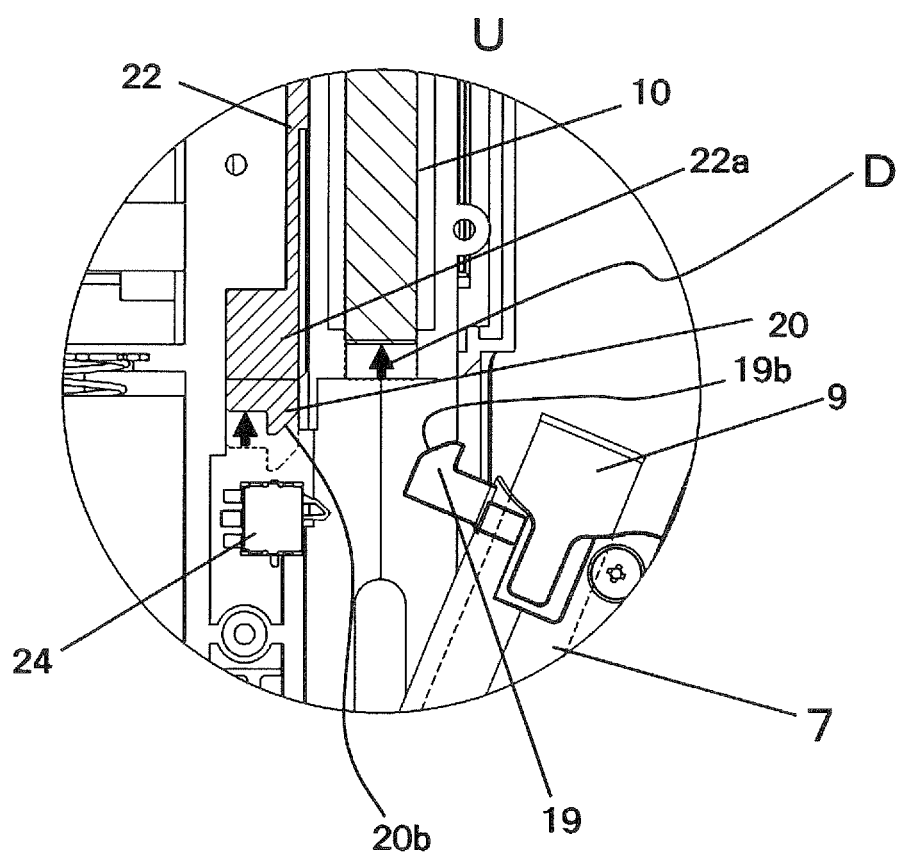
FIG. 8 is a detail view of the main components of the pharmaceutical injection device pertaining to an embodiment of the present invention.

Next, the operation of the cartridge holder 7 during ejection will be described through reference to FIGS. 7 and 8. FIG. 7 is a configuration diagram of the state during ejection of the cartridge holder 7 of the pharmaceutical injection device in this embodiment. FIG. 8 is a detail view of the U portion in FIG. 7.

When the pharmaceutical administration (injection) operation described in FIGS. 5 and 6 above is complete, and there is no more pharmaceutical in the pharmaceutical cartridge 9, the cartridge holder 7 must be opened up and the pharmaceutical cartridge 9 replaced.

More specifically, in FIG. 5, when the piston 10 has moved the gasket 41 of the pharmaceutical cartridge 9 to the distal end, and all of the pharmaceutical in the pharmaceutical cartridge 9 has thereby been injected, the piston 10 is retracted to its origin position by the piston drive mechanism 100.

After this, the pharmaceutical cartridge 9 needs to be replaced, so as shown in FIGS. 5 and 6, the piston 10 is moved upward beyond the origin position (see FIG. 4b).

At this point, the protrusion 10b at the upper end of the piston 10 is in contact with the protrusion 22b of the lever 22, so the lever 22 moves upward together.

The ejector pawl 20 attached to the lower end of the lever 22 also moves upward together, while compressing the biased spring 21. This operation disengages the latched component 19 and the ejector pawl 20.

At this point, the cartridge holder 7 opens outward from the main body case 1 under the biasing force of the ejector spring 18, with the axial support 17 as the fulcrum.

Whether or not the cartridge holder 7 has opened up here can be detected by an opening/closing detector switch 24 provided near the ejector pawl 20 (see FIG. 4a, etc.).

For instance, when the cartridge holder 7 is closed, the opening/closing detector switch 24 is pushed down by the cartridge holder 7 to the ON state, and it is detected that the cartridge holder 7 has been closed. When the cartridge holder 7 has been opened, the pressing down of the opening/closing detector switch 24 by the cartridge holder 7 is released to the OFF state, and it is detected that the cartridge holder 7 is open.

Before this eject operation is performed, for the sake of safety, the injection needle 16 attached to the injection needle mounting component 3 must be removed, so a message prompting the user to remove the injection needle 16 is displayed on the display component 5 provided to the front face of the main body case 1.

As to the removal of the injection needle 16, the needle detector switch 15 can detect that the injection needle 16 has been removed.

Operation During Closing of Cartridge Holder 7

Figure 9:
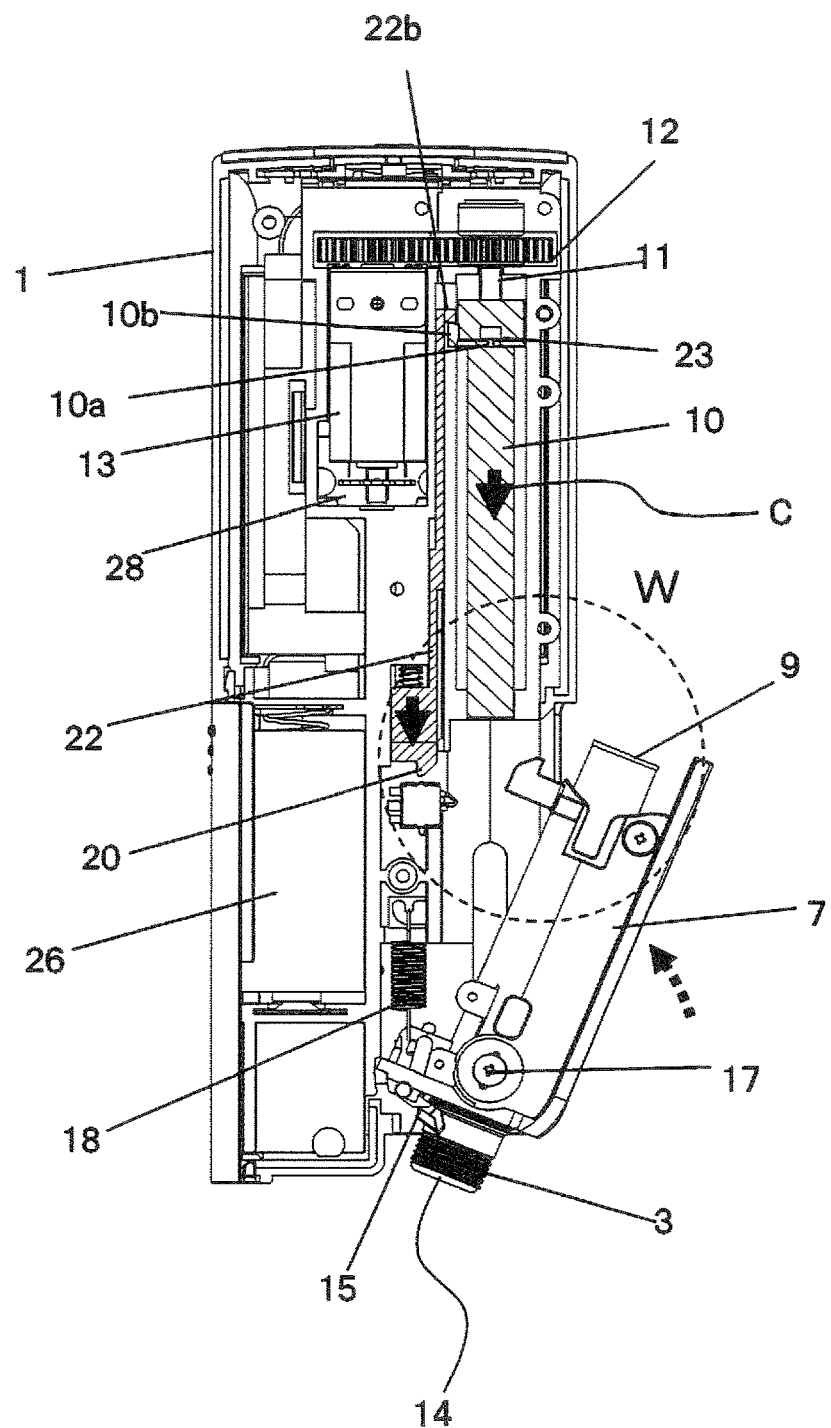
FIG. 9 is a front cross section of the internal configuration of the pharmaceutical injection device pertaining to an embodiment of the present invention.
Figure 10:
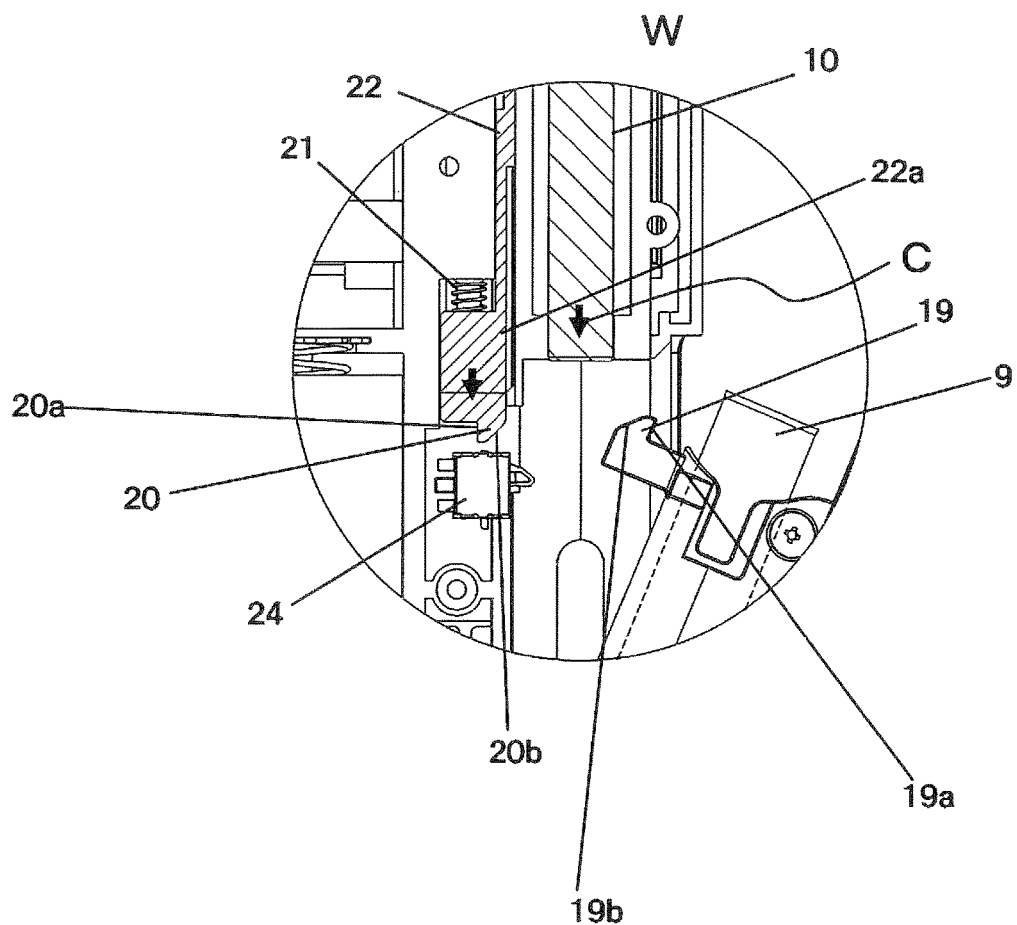
FIG. 10 is a detail view of the main components of the pharmaceutical injection device pertaining to an embodiment of the present invention.

FIG. 9 is a cross sectional configuration diagram of the pharmaceutical injection device in the closing of the cartridge holder 7. FIG. 10 is a detail view of the W portion in FIG. 9.

FIGS. 9 and 10 show a state in which the piston 10 has been moved to its origin position after the ejection operation described with FIGS. 7 and 8 above.

At this point, as the piston 10 is returning to its origin position, the lever 22 and the ejector pawl 20 also move downward, and the piston 10 moves to its origin position and goes back to the initial state (see FIG. 3).

However, since the cartridge holder 7 is still open here, the latched component 19 and the ejector pawl 20 are not engaged.

After this, when the pharmaceutical cartridge 9 is replaced and the cartridge holder 7 is moved so as to close toward the main body case 1 side, the sloped part 19b of the latched component 19 moves up and over the sloped part 20b of the ejector pawl 20 as shown in FIG. 10, and finally the latched component 19 and the ejector pawl 20 engage and are held in that state.

That is, the piston 10 goes back to its initial state, and the cartridge holder 7 holding the new pharmaceutical cartridge 9 is held inside the main body case 1.

Control Blocks

Figure 11:
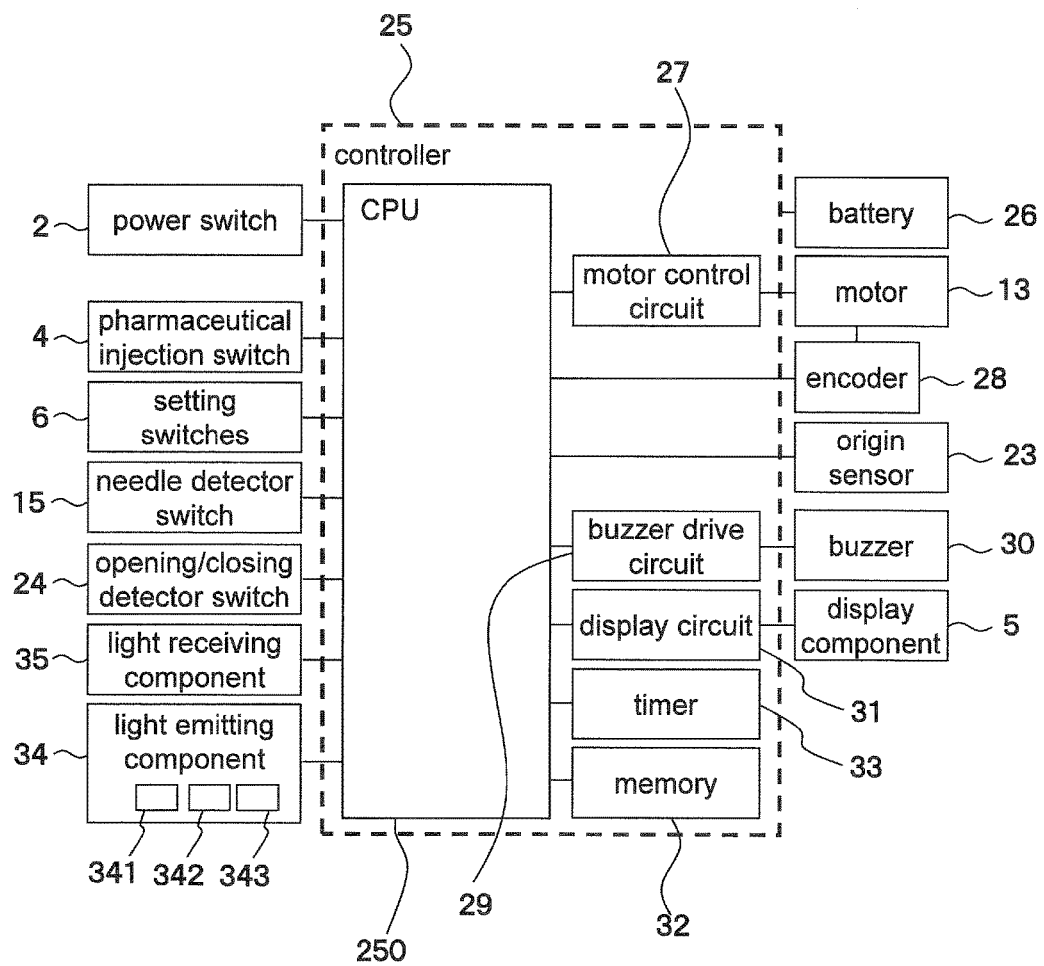
FIG. 11 is a control block diagram of the pharmaceutical injection device pertaining to an embodiment of the present invention.

FIG. 11 is a block diagram of the electrical circuit within the main body case 1 of the pharmaceutical injection device, and the surrounding area. A controller 25 has a CPU 250, is connected to various input/output interfaces and drive systems, and controls these.

More specifically, in regard to operation components, the CPU 250 of the controller 25 is connected to the power switch 2, the pharmaceutical injection switch 4, the setting switches 6, and so forth, and checks the input of various control switches.

In regard to detecting states, the CPU 250 of the controller 25 is connected to the needle detector switch 15, which detects the attachment state of the injection needle 16, the opening/closing detector switch 24, which detects whether the cartridge holder 7 is open or closed, and, as will be discussed in detail below, a light emitting component 34 and a light receiving component 35 for identifying the pharmaceutical cartridge 9.

In regard to the drive system of the piston 10, the motor 13 that drives the piston 10 is connected to the CPU 250 inside the controller 25 via a dedicated motor control circuit 27 that controls the motor. An encoder 28 that senses position information about the piston 10 is connected to the motor 13, and outputs pulses corresponding to the rotation of the motor 13 to the CPU 250. The CPU 250 counts the pulses outputted by the encoder 28, and calculates the amount of movement by the piston 10. Furthermore, the origin sensor 23, which senses the origin position of the piston 10, is connected to the CPU 250, and the CPU 250 uses the output of the encoder 28 and the output of the origin sensor 23 to recognize the current piston position.

A memory 32 is connected to the CPU 250, and holds this recognized current piston position as piston position information. The piston position information is a positive or negative numerical value. When the piston position information is zero, it means that the piston 10 is in its origin position. When the piston position information is positive, it means that the piston 10 is lower than the origin position.

Conversely, when the piston position information is negative, it means that the piston 10 is higher than the origin position. The absolute value of the piston position information refers to the movement distance from the origin position.

More specifically, when the rear end side of the protrusion 10a provided to the piston 10 crosses the origin sensor 23, the CPU 250 determines that the piston 10 is in its origin position, and resets the piston position information stored in the memory 32 to zero. The CPU 250 then updates the value by adding or subtracting one piece of piston position information according to the drive direction of the motor 13, each time the encoder 28 connected to the motor 13 outputs one pulse. Thus, the CPU 250 can always use the piston position information held in the memory 32 to recognize the current piston position. The memory 32 is constituted by a nonvolatile memory such as an EEPROM, so the piston position information stored in the memory 32 will be preserved even if power to the device is cut off. This piston position information is always reset to zero when the rear end side of the protrusion 10a provided to the piston 10 crosses the origin sensor 23. That is, the origin sensor 23 is used to correct the piston position. The CPU 250 monitors the output of the origin sensor 23, and when the error with respect to zero in the piston position information stored in the memory 32 when the origin sensor 23 has sensed the origin position exceed the predetermined threshold, since there is the possibility of some kind of trouble occurring in the operation of the device, processing is performed to display a warning on the display component 5 and halt the operation, etc.

In addition, in the controller 25 a buzzer 30 that apprises the user that an error has occurred is connected to the CPU 250 via a buzzer drive circuit 29 that controls this buzzer. In the controller 25 the display component 5, which displays various messages, numerical values, etc., is connected to the CPU 250 via a dedicated display circuit 31 that controls the display component 5. The memory 32 that holds dosages, injection data, and so forth, and a timer 33 that measures the elapsed time are built into the controller 25, and are connected to the CPU 250. Also, a battery 26 that serves as the power supply of the device is also built in, and is connected to the controller 25.

Identifier 300 for Identifying Type of Pharmaceutical Cartridge 9

A feature of this embodiment is that the type of pharmaceutical cartridge 9 held in the cartridge holder 7 is identified. The pharmaceutical injection device in this embodiment comprises an identifier 300 to identify the type of pharmaceutical cartridge 9.

Figure 12:
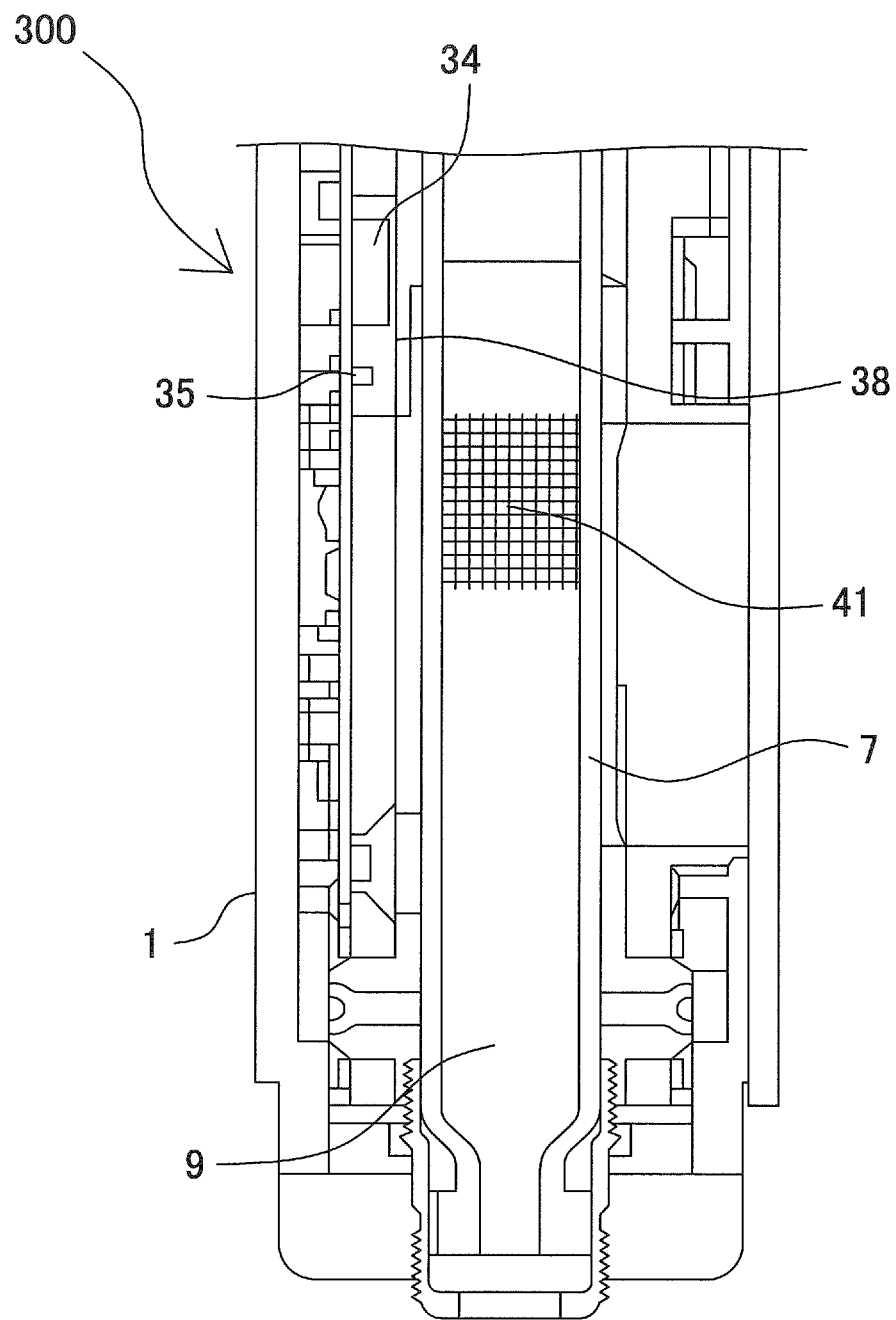
FIG. 12 is a cross section of the pharmaceutical injection device pertaining to an embodiment of the present invention.
Figure 13:
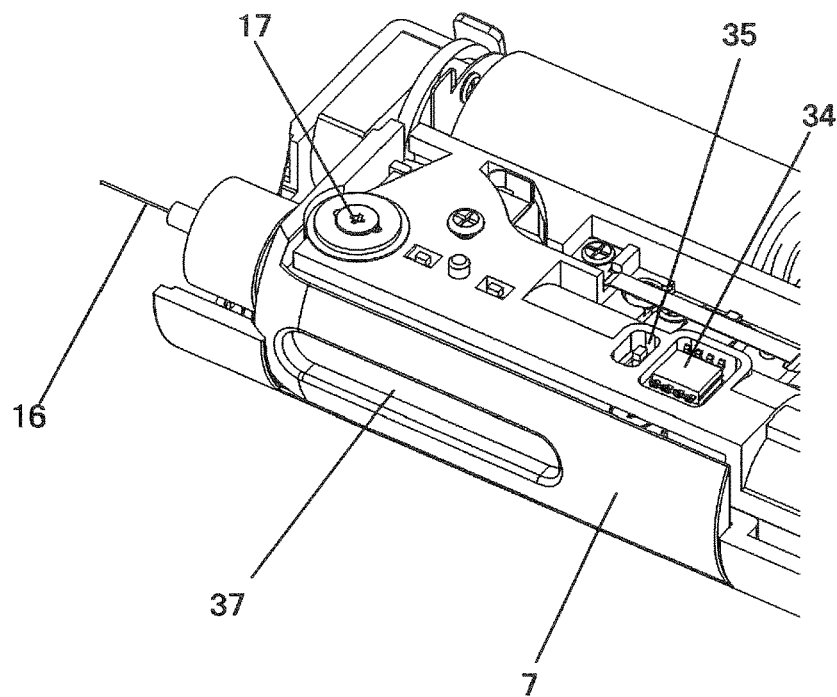
FIG. 13 is an oblique view of the pharmaceutical injection device pertaining to an embodiment of the present invention.
Figure 14:
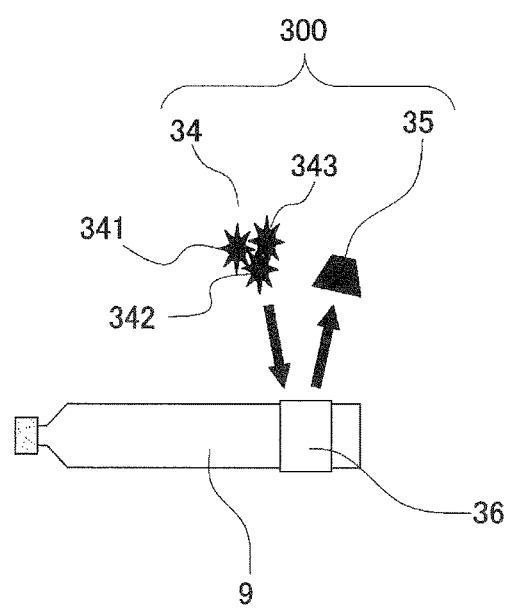
FIG. 14 is a simplified configuration diagram showing part of the pharmaceutical injection device pertaining to an embodiment of the present invention.

FIG. 12 shows the configuration near the cartridge holder 7, and is a cross section of the pharmaceutical injection device as seen from a confirmation window 37 side. FIG. 13 is an oblique view of the area near the cartridge holder 7. FIG. 14 is a simplified view of the pharmaceutical cartridge 9 and the identifier 300.

More specifically, the identifier 300 in this embodiment has the light emitting component 34 and the light receiving component 35. As shown in FIGS. 12 to 14, the configuration is such that light from the light emitting component 34 is shined on the pharmaceutical cartridge 9 held in the cartridge holder 7, and reflected light from the pharmaceutical cartridge 9 is received by the light receiving component 35.

The light emitting component 34 has three-color LEDs (a red LED 341, which is a red light emitting element, a green LED 342, which is a green light emitting element, and a blue LED 343, which is a blue light emitting element (see FIGS. 11 and 14)). These colored light emitting elements emit light while being switched in order, the light from the light emitting elements of the various colors shines on the pharmaceutical cartridge 9, and the reflected light is sequentially received by the light receiving component 35.

The light receiving component 35 also senses the amount of light reflected from the pharmaceutical cartridge 9 for each of the colors; a photosensor is used, for example.

As shown in FIG. 14, a color label 36, which indicates the type, amount, etc., of the pharmaceutical that fills the pharmaceutical cartridge 9, is wound in a strip around the outside of the pharmaceutical cartridge 9. As shown in FIG. 14, the light from the light emitting component 34 is shined toward the color label 36, and light reflected by this color label 36 is sensed by the light receiving component 35.

In this embodiment, in a state in which the pharmaceutical cartridge 9 has been inserted through the insertion opening 8 into the cartridge holder 7, a portion of the color label 36 on the pharmaceutical cartridge 9 is exposed above the insertion opening 8. In this state, as shown in FIG. 2, even when the cartridge holder 7 is closed, a portion of the color label 36 on the pharmaceutical cartridge 9 will be exposed inside the main body case 1, above the insertion opening 8 of the cartridge holder 7 (see FIG. 4a). In FIG. 4a, the light emitting component 34 and the light receiving component 35 are indicated by dotted lines.

The light from the light emitting component 34 is then shined on the color label 36 in this exposed state, and the reflected light is received by the light receiving component 35.

That is, the light emitting component 34 and the light receiving component 35 are in a state of being fixed in their disposition within the main body case 1, and do not move when the cartridge holder 7 is opened or closed.

As shown in FIG. 12, a dust-proof film 38 is provided to the front side (the pharmaceutical cartridge 9 side) of the light emitting component 34 and the light receiving component 35 thus fixed within the main body case 1. Consequently, dust and dirt will not directly adhere to the light emitting component 34 and the light receiving component 35. Naturally, a dust-proof film 38 is used that has no filtering characteristics with respect to visible light. Consequently, the above-mentioned red, green, and blue light is emitted from the light emitting component 34 and shines on the color label 36 of the pharmaceutical cartridge 9.

In this example, the color label 36 is attached to the pharmaceutical cartridge 9, but if the pharmaceutical cartridge 9 itself is colored, then light from the light emitting component 34 may be shined directly on this pharmaceutical cartridge 9, and the reflected light may be sensed by the light receiving component 35.

In other words, in this embodiment, the controller 25 is connected to the light emitting component 34, which shines light of different colors on the pharmaceutical cartridge 9 disposed in the cartridge holder 7, and to the light receiving component 35, which receives light shined from the light emitting component 34 onto the pharmaceutical cartridge 9 and reflected by the pharmaceutical cartridge 9 (see FIG. 11).

The controller 25 also successively shines light of different colors from the light emitting component 34 onto the pharmaceutical cartridge 9, and identifies the type of pharmaceutical cartridge 9 on the basis of the amount of light received by the light receiving component 35 for each color.

Therefore, even if dust or dirt should adhere to the light receiving component 35, when light of different colors is successively shined from the light emitting component 34 onto the pharmaceutical cartridge 9, the amount of light received by the light receiving component 35 for each color will just decrease as the overall sensed level. In such a state in which just the sensed level decreases uniformly for all of the colors, the controller 25 will still be able to properly identify the type of pharmaceutical cartridge 9 from the amount of light of each color.

As shown in FIGS. 1 and 13, the cartridge holder 7 is provided with a confirmation window 37 for confirming the state of the pharmaceutical cartridge 9 housed in the interior of the cartridge holder 7. This point will now be described in detail.

With the pharmaceutical injection device in this embodiment, whether or not there is a pharmaceutical cartridge 9, how much pharmaceutical is left in this pharmaceutical cartridge 9, and so forth can be confirmed through the confirmation window 37 provided to the main body case 1.

Also, the controller 25 confirms the remaining amount of pharmaceutical on its own. The operation of the pharmaceutical injection device in this embodiment, including this confirmation of the remaining amount, will now be described through reference to a flowchart.

Operation of Pharmaceutical Injection Device

Figure 19:
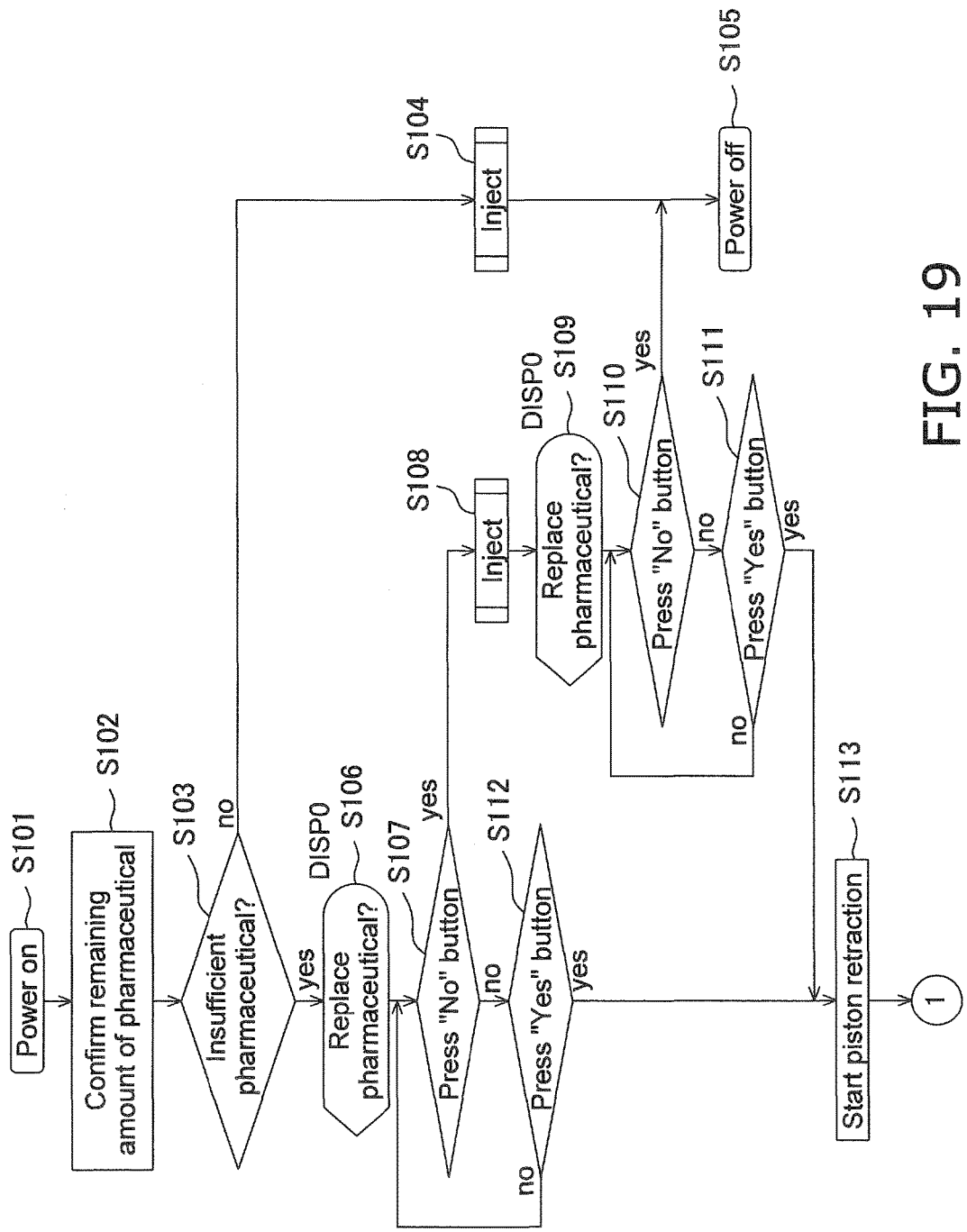
FIG. 19 is an operational flowchart of the pharmaceutical injection device pertaining to an embodiment of the present invention.

FIG. 19 is a flowchart of the operation of pharmaceutical injection device pertaining to this embodiment in which the amount of remaining pharmaceutical is confirmed. FIGS. 15a to 15k are diagrams of the display on the pharmaceutical injection device. The parts marked DISPn (where n is a numeral) in the flowchart means that the (n) display in FIGS. 15a to 15k is given in this display operation. For instance, S106 in FIG. 19 is marked DISP0, and in S106 the display of FIG. 15a marked DISP0 (out of FIGS. 15a to 15k) is given.

Operation of Confirming Remaining Amount of Pharmaceutical

More specifically, when the power switch 2 is turned on (S101 in FIG. 19), the controller 25 uses the encoder 28 to sense position information about the piston 10, and thereby confirms the remaining amount of pharmaceutical (S102 in FIG. 19).

If it is concluded from this remaining amount confirmation that sufficient pharmaceutical remains, the controller 25 drives the motor 13 to push the piston 10 in the direction of the injection needle 16. This causes the pharmaceutical to be injected into the body, after which the power is switched off (S103, S104, and S105 in FIG. 19).

Figure 15:
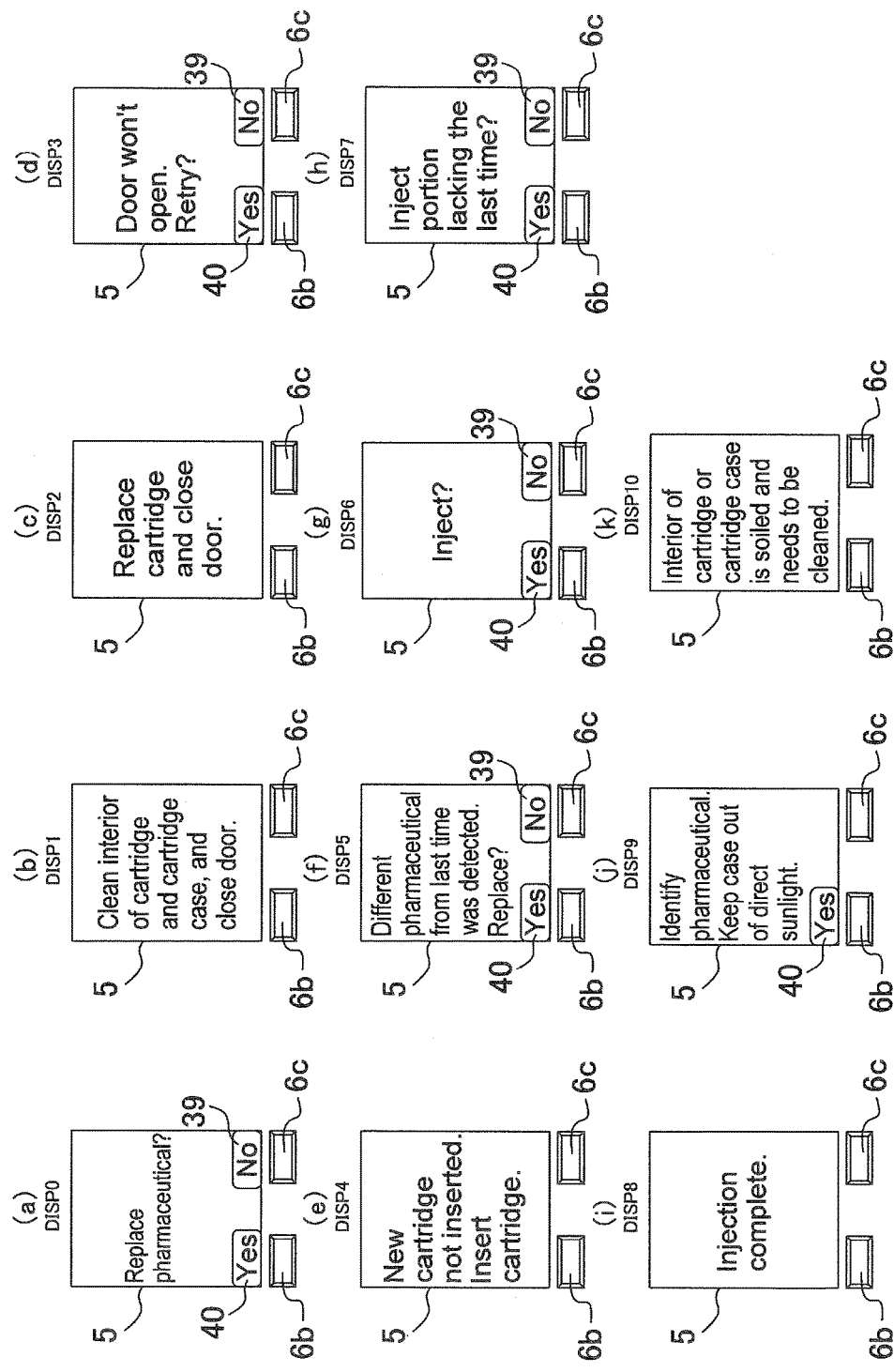
FIGS. 15a to 15k are diagrams of the display component of the pharmaceutical injection device pertaining to an embodiment of the present invention.

In S103 in FIG. 19, if it is concluded that there is insufficient pharmaceutical (the remaining pharmaceutical is less than the amount needed for a single injection), the controller 25 causes the display component 5 to display a message of "Replace pharmaceutical?," as shown in FIG. 15a (S106 in FIG. 19). As shown in FIG. 15a, a "Yes" display 40 is given on the display component 5 above the setting switch 6b on the left side, and a "No" display 39 is given on the display component 5 above the setting switch 6c on the right side. Specifically, in the state in FIG. 15a, "Yes" is selected by pressing the setting switch 6b on the left, and "No" is selected by pressing the setting switch 6c on the right. The same applies to FIGS. 15d, 15f, 15g, and 15h discussed below. FIG. 15j differs from FIG. 15a in that the "No" display 39 does not appear.

If the user who sees the display shown in FIG. 15a decides to go ahead and inject the pharmaceutical remaining in the pharmaceutical cartridge 9, and then replace the pharmaceutical cartridge 9 with a new one and inject additional pharmaceutical, he presses the setting switch 6c under the "No" display 39 on the display component 5 as shown in FIG. 15a (S107 in FIG. 19).

The controller 25 then drives the motor 13 to push the piston 10 in the direction of the injection needle 16, and this causes the pharmaceutical to be injected into the body (S108 in FIG. 19).

After this, the controller 25 again causes the display component 5 to give a display of "Replace pharmaceutical?" (S109 in FIG. 19).

If once again the user presses the setting switch 6c under the "No" display 39 on the display component 5, the power is switched off (S110 and S105 in FIG. 19).

In contrast, if the user presses the setting switch 6b under the "Yes" display 40 on the display component 5 in FIG. 15a, an operation to replace the pharmaceutical cartridge 9 is executed (S111 in FIG. 19).

This replacement operation is also executed when the user presses the setting switch 6b under the "Yes" display 40 in S106 in FIG. 19 (S112 in FIG. 19).

Pharmaceutical Cartridge Replacement Operation

This operation to replace the pharmaceutical cartridge 9 is commenced from an operation in which the controller 25 reverses the drive of the motor 13 to retract the piston 10 (S113 in FIG. 19).

As discussed above, in this embodiment the opening up of the pharmaceutical cartridge 9 is performed automatically when the piston 10 retracts to its origin position.

More specifically, as discussed above, the origin sensor 23, which senses the origin position of the piston 10, is provided on the rear end side of the piston 10 (the upper end side in FIG. 1). Here, the protrusion 10b on the rear end part of the piston 10 hits the protrusion 22b only when the piston 10 retracts higher than this origin position, so the entire lever 22 retracts together (moves upward in FIGS. 1 and 2) (see FIG. 4b).

Meanwhile, during pharmaceutical injection (the state in FIGS. 5 and 6), when the piston 10 moves downward (that is, moves lower than the origin position), the protrusion 22b on the upper end side of the lever 22 moves downward along with the protrusion 10b on the rear end part of the piston 10 under the biasing force of the spring 21. However, the lever 22 stops at the position shown in FIG. 3 (see the dotted line position in FIG. 8), and will not descend any further, so when the piston 10 descends further, the protrusion 22b on the upper end side of the lever 22 separates from the protrusion 10a of the piston 10.

That is, the latched component 19 provided inside the main body case 1 and the ejector pawl 20 that is adjacent to the protrusion 22a on the lower end side of the lever 22 engage, and this maintains the cartridge holder 7 in a closed state.

Specifically, the ejector pawl 20 attached to the protrusion 22a on the lower end side of the lever 22 is such that after the piston 10 has completed the injection of all of the pharmaceutical in the pharmaceutical cartridge and returned to its origin position as shown in FIG. 8, and then moves further upward, this disengages the latched component 19 from the protrusion 22b of the ejector pawl 20, and the cartridge holder 7 is opened up (that is, the cartridge holder 7 is always biased in the opening direction by the ejector spring 18 (see FIG. 7)).

Figure 20:
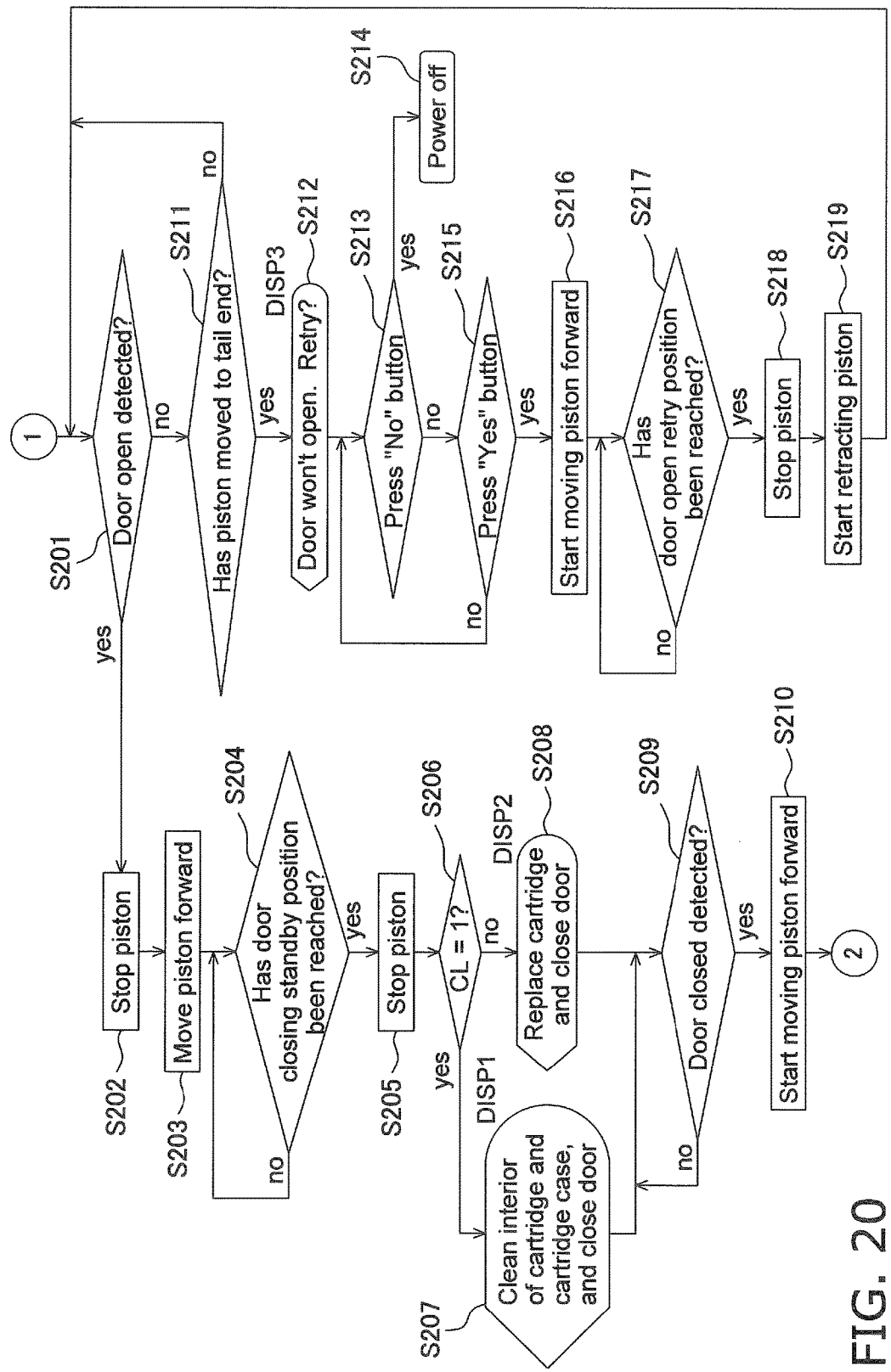
FIG. 20 is an operational flowchart of the pharmaceutical injection device pertaining to an embodiment of the present invention.

Whether or not the cartridge holder 7 (also called a door) has been opened can be detected by the opening/closing detector switch 24 provided near the ejector pawl 20 (S201 in FIG. 20).

The controller 25 then stops the reverse operation of the motor 13 (the upward movement of the piston 10) (S202 in FIG. 20). Next, the controller 25 moves the piston 10 forward until the ejector pawl 20 is in the state in FIG. 10 (lower end position), and stops the operation of the motor 13 in this state (S203, S204, and S205 in FIG. 20). The encoder 28 detects that the ejector pawl 20 has entered the state in FIG. 10. The lower end position of the ejector pawl 20 shown in FIG. 10 is also called the position where the system waits for the cartridge holder 7 to be closed, that is, a door closing standby position.

The controller 25 then causes the display component 5 to give the display shown in FIG. 15b or 15c on the basis of information about whether or not dirt was detected from the data sensed by the light receiving component 35. This dirt detection by the light receiving component 35 will be described in detail below, but if dirt is detected, data of CL=1 is stored in the memory 32.

When this data of CL=1 is recorded to the memory 32, the controller 25 causes the display component 5 to give a display of "Clean interior of cartridge and cartridge case, and close door" as shown in FIG. 15b (S206 and S207 in FIG. 20).

When this data of CL=1 is not recorded to the memory 32, the controller 25 causes the display component 5 to give a display of "Replace cartridge and close door" as shown in FIG. 15c (S206 and S208 in FIG. 20).

After this, the pharmaceutical cartridge 9 is replaced as in FIG. 2, and the cartridge holder 7 is closed as in FIG. 1, at which point this state is detected by the opening/closing detector switch 24 (S209 in FIG. 20), after which the motor 13 moves the piston 10 forward until it reaches the gasket 41 of the pharmaceutical cartridge 9 (S210 in FIG. 20).

Figure 21:
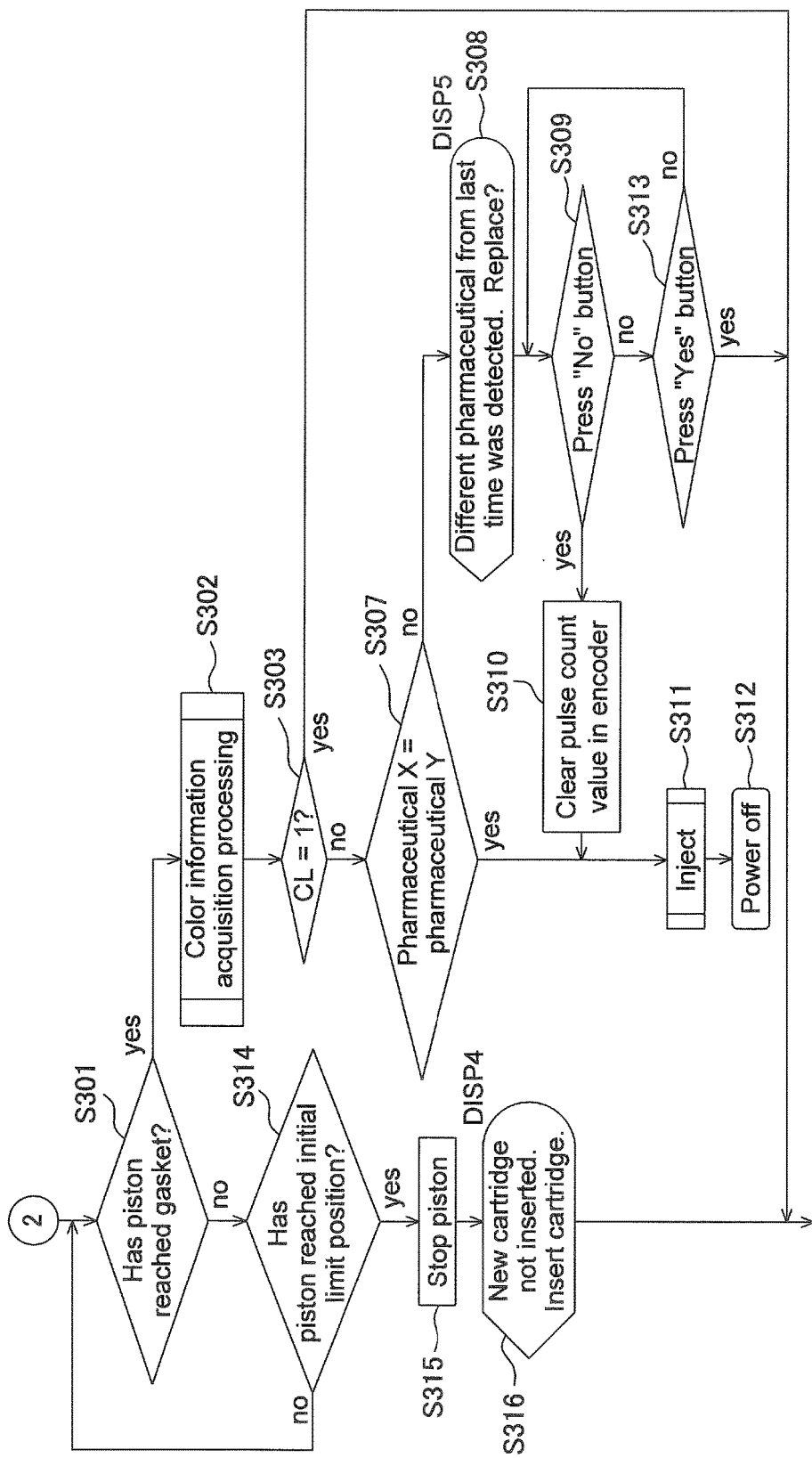
FIG. 21 is an operational flowchart of the pharmaceutical injection device pertaining to an embodiment of the present invention.

The encoder 28 detects that the piston 10 has reached the gasket 41 (S301 in FIG. 21), and then the type of the newly installed pharmaceutical cartridge 9 is identified (S302 in FIG. 21).

Operation to Identify Type of Pharmaceutical Cartridge

Figure 23:
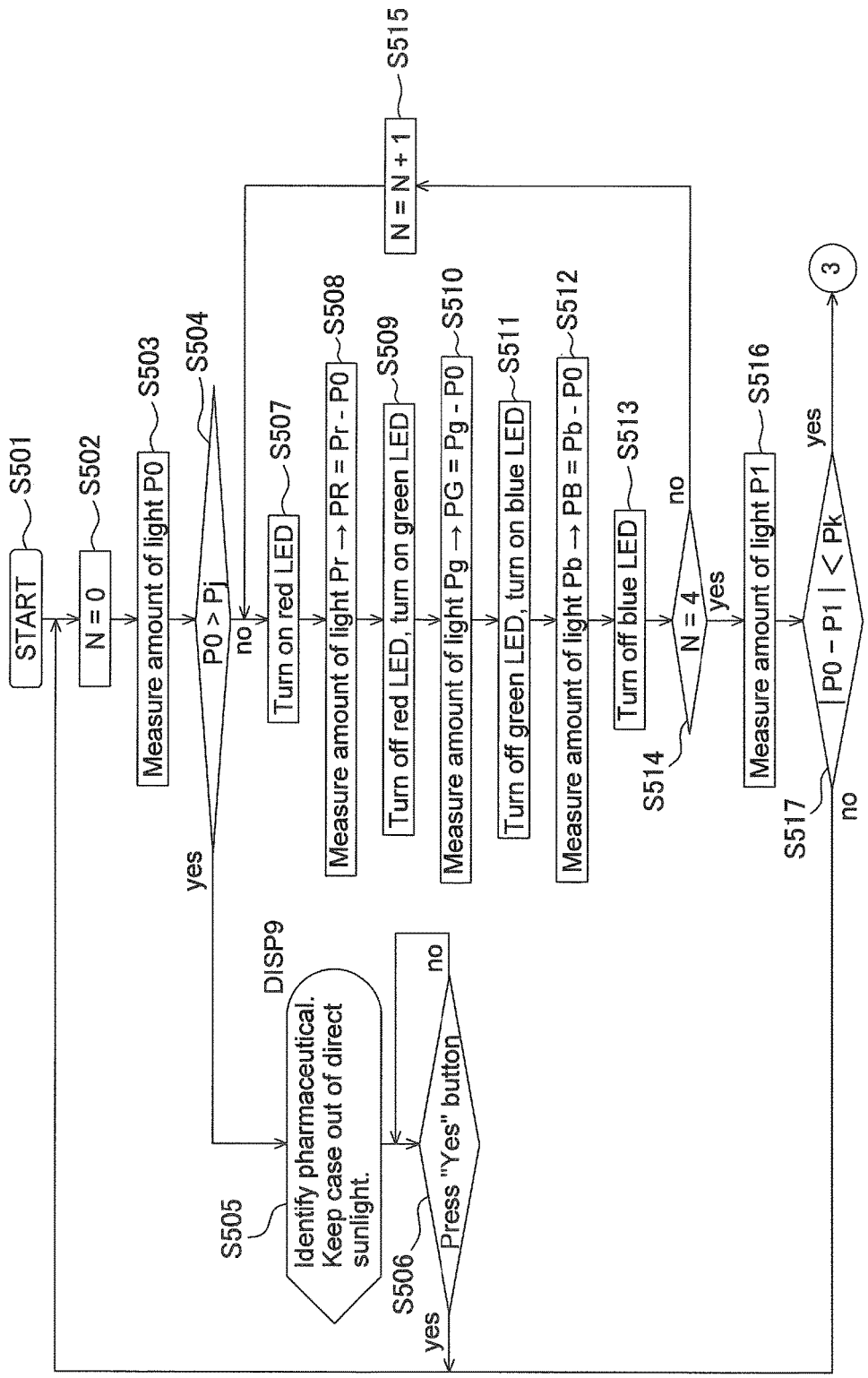
FIG. 23 is an operational flowchart of the pharmaceutical injection device pertaining to an embodiment of the present invention.
Figure 24:
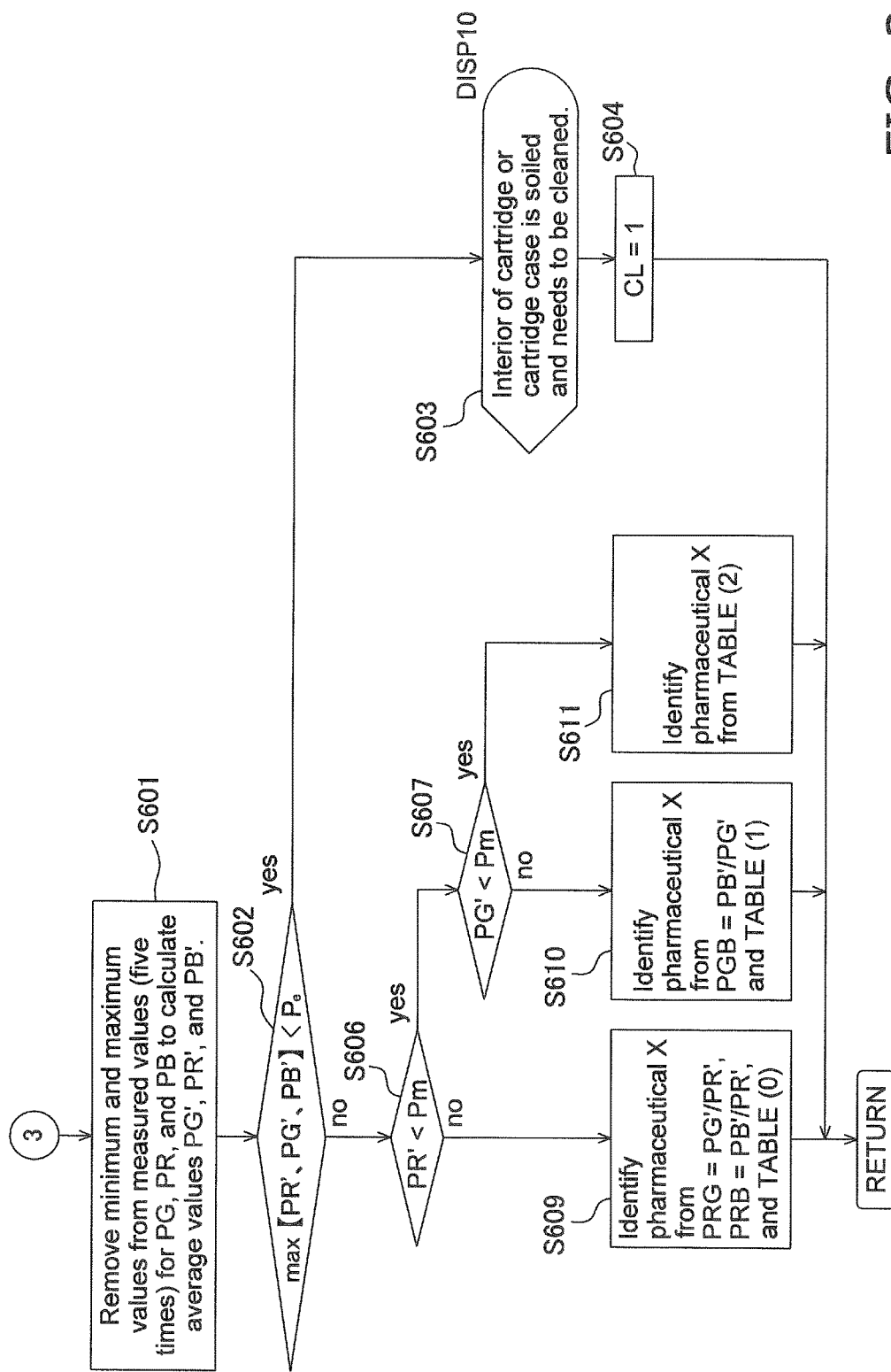
FIG. 24 is an operational flowchart of the pharmaceutical injection device pertaining to an embodiment of the present invention.

FIGS. 23 and 24 are flowcharts of the operation to identify the type of pharmaceutical cartridge in the pharmaceutical injection device of this embodiment.

This identification of the type of the pharmaceutical cartridge 9 is executed by the operation in FIGS. 23 and 24. That is, if the controller 25 identifies the type of the pharmaceutical cartridge 9 by measuring five times, for example, after the start the N recorded to the memory 32 is set to zero, and the amount of light P0 when the light emitting component 34 is off is measured by the light receiving component 35 (S501, S502, and S503 in FIG. 23).

It is then determined whether or not this amount of light is greater than Pj (external light determination threshold) (S504).

That is, since the main body case 1 is provided with the confirmation window 37 used for confirming the pharmaceutical cartridge 9, there may be situations when external light reaches the light receiving component 35 through this window. If the external light is too strong, this results in a situation in which the light receiving component 35 cannot function the identification properly, so in the case of strong external light, that is, if the amount of light received by the light receiving component 35 is too strong, the controller 25 causes the display component 5 to give a display of "Identify pharmaceutical. Keep case out of direct sunlight" as shown in FIG. 15j (S504 and S505 in FIG. 23).

If the user presses the setting switch 6b under the "Yes" display 40, the flow returns to S502 in FIG. 23 (S506 and S502 in FIG. 23).

If the device is being used in a suitable place (where strong external light cannot get it), the controller 25 causes the red LED 341 of the light emitting component 34 to emit light after S504 in FIG. 23, and red light is shined at the color label 36 on the pharmaceutical cartridge 9 (S507 in FIG. 23).

The reflected light from the color label 36 is sensed by the light receiving component 35 here, and the amount of red light is measured (S508 in FIG. 23).

The amount of light at this point is the value obtained by subtracting the external light P0.

That is, in S503 in FIG. 23, since the light emitting component 34 is off and the amount of light at that point is being received by the light receiving component 35, the amount of light P0 caused by external light is measured by the light receiving component 35 at this point.

Therefore, in S508 in FIG. 23, the amount of light PR when the red LED 341 emits light is Pr-P0, obtained by subtracting the amount of light P0 caused by external light from the amount of light Pr that could be measured by the light receiving component 35 at this point.

Then, the controller 25 turns off the red LED 341 and lights the green LED 342, and the amount of light at this point is sensed by the light receiving component 35 (S509 and S510 in FIG. 23).

The amount of light at this point is the value obtained by subtracting the external light P0.

That is, in S503 in FIG. 23, the light emitting component 34 is turned off, and the amount of light at that point is received by the light receiving component 35, so the amount of light P0 caused by external light is measured by the light receiving component 35 at this point.

Therefore, in S510 in FIG. 23, the amount of light PG when the green LED emits light is Pg-P0, obtained by subtracting the amount of light P0 caused by external light from the amount of light Pg that could be measured by the light receiving component 35 at this point.

Then, the controller 25 turns off the green LED 342 and lights the blue LED 343, and the amount of light at that point is sensed by the light receiving component 35 (S511 and S512 in FIG. 23).

The amount of light at this point is the value obtained by subtracting the external light P0.

That is, in S503 in FIG. 23, the light emitting component 34 is turned off, and the amount of light at that point is received by the light receiving component 35, so the amount of light P0 caused by external light is measured by the light receiving component 35 at this point.

Therefore, in S512 in FIG. 23, the amount of light PB when the blue LED 343 emits light is Pb-P0, obtained by subtracting the amount of light P0 caused by external light from the amount of light Pb that could be measured by the light receiving component 35 at this point.

After this, the blue LED 343 is turned off (S513 in FIG. 23), and it is then determined whether or not measurement has been done five times (N=4) (S514 in FIG. 23).

If the number has not reached five times, 1 is added to the number of times, this is recorded in the memory 32 (S515 in FIG. 23), and the operation from S507 to S515 in FIG. 23 is repeated again. The amount of light is measured five times by repeating the operation from S507 to S515 until N=5. After measurement is finished, the amount of light P1 in a state in which the light emitting component 34 has been turned off is measured (S516 in FIG. 23).

If the absolute value obtained by subtracting the amount of light P1 from the amount of light P0 caused by external light is less than an amount of external light change determination threshold Pk, the flow proceeds to the color determination shown in FIG. 24 (S517 in FIG. 23). The above-mentioned steps S501 to S517 correspond to an example of the amount of light measurement process.

In S517 in FIG. 23, if the absolute value obtained by subtracting the amount of light P1 from the amount of light P0 caused by external light is greater than external light change determination threshold Pk, there is the possibility that there is a significant change in the external light and the amount of light has not been measured five times in a row at the proper place, so the flow returns to S502 in FIG. 23.

Also, in S517 in FIG. 23, if it has been determined that the amount of light has been properly measured, the operation shown in S601 in FIG. 24 is executed.

That is, since the amounts of light PR, PG, and PB for the above-mentioned five times are recorded in the memory 32, the controller 25 removes the minimum and maximum values for each color, and calculates the average value for each color from the remaining three measurement values (S601 in FIG. 24). Here, we shall let PR' be the average value for the three amounts of light PR, PG' be the average value for the three amounts of light PG, and PB' be the average value for the three amounts of light PB.

If the largest average value for each color is less than a dirt determination level Pe, soiling is suspected, so the controller 25 causes the display component 5 to give a display of "Interior of cartridge or cartridge case is soiled and needs to be cleaned" as shown in FIG. 15k, and records CL=1 in the memory 32 (S603 and S604 in FIG. 24).

In contrast, in S602 in FIG. 24, if the largest average value for each color is greater than a dirt determination level Pe, it is assumed that proper detection has been performed, and determination of the color components is then carried out. If CL=1 has been recorded to the memory 32, and the largest average value for each color is greater than a dirt determination level Pe, it is assumed that the soiling has been eliminated, and the record of CL=1 is erased.

First, it is determined whether the average value PR' is less than a minimum brightness Pm (S606 in FIG. 24). That is, it is determined whether or not a red component is present. The dirt determination level Pe is a value greater than the minimum brightness Pm.

If no red component is present, it is determined whether the average value PG' is less than the minimum brightness Pm (S607 in FIG. 24). That is, it is determined whether or not a green component is present.

If the average value PR' is greater than the minimum brightness Pm in S606 in FIG. 24, pharmaceutical X is specified by the TABLE(0) 42 (shown in FIG. 16) stored in the memory 32 and (S609 in FIG. 24).

In this embodiment, the following process is executed by the controller 25 to specify the pharmaceutical X. For example, if the output of the light receiving component 35 is digitized by a 256-gradient A/D converter, the output of the light receiving component 35 is digitized in values of 0 to 255. PRG, which is the ratio of red and green (green/red), PRB, which is the ratio of red and blue (blue/red), PGB, which is the ratio of green and blue (blue/green), and PB', which is the brightness of the color blue, are used in identifying the pharmaceutical X. FIG. 16 shows an example of the values of PRG, PRB, PGB, and PB' in the identification of 19 colors. The values shown in FIG. 16 are an example of reference data.

Using "pharmaceutical 6" in FIG. 16 as an example, when the brightness of the color red is at or above the minimum brightness Pm, if PRG is 0.5 and PRB is 1, the controller 25 determines that the pharmaceutical cartridge 9 held in the cartridge holder 7 is "pharmaceutical 6." To obtain this result, a color label may be used having the components of R=252, G=126, and B=252 as the label for the pharmaceutical.

In contrast, in S606 in FIG. 24, when the average value PR' is at or under the minimum brightness Pm, the condition in S607 in FIG. 24 is that the average value PG' is greater than the minimum brightness Pm, and the pharmaceutical X is specified on the basis of the TABLE(1) 43 (shown in FIG. 17) stored in the memory 32 (S610 in FIG. 24).

That is, the pharmaceutical X is specified from the average value PB'/the average value PG'.

In S607 in FIG. 24, if the average value PG' is also less than the minimum brightness Pm, the pharmaceutical X is specified by the TABLE(2) 44 shown in FIG. 18 (S611 in FIG. 24). Here, in order for the control flow to go to S607, either PR', PG', or PB' must be at or above Pe in the determination in S602. Therefore, if it is determined that there is no red or green component (if it is determined that PR' and PG' are less than the minimum brightness Pm), the average value PB' will be a value greater than the dirt determination level Pe. That is, when control moves to S611, the average value PB' is greater than the minimum brightness Pm, so the determination in S606 and S607 is not provided for PB'. When the control moves to S611, only the blue component is present, and the controller 25 determines that the pharmaceutical cartridge 9 held in the cartridge holder 7 is "pharmaceutical 18" on the basis of the TABLE (2) 44.

If the pharmaceutical can thus be specified from color sensing of the color label 36, the flow proceeds again to S303 in FIG. 21. The above-mentioned S601, S606, S607, and S609 to S611 correspond to an example of a determination process. The above-mentioned S601, S602 to S604, and S207 correspond to an example of a warning output process.

In S303 in FIG. 21, CL=1 and the flow moves to S306 when soiling is detected in S604 in FIG. 24, and when color sensing is executed in FIG. 24, the control moves to S307 in FIG. 21.

In S307 in FIG. 21, it is determined whether or not the pharmaceutical (X) specified this time is the same as the pharmaceutical (Y) used the last time.

In S307 in FIG. 21, if the pharmaceutical (X) is different from the pharmaceutical (Y), the controller 25 causes the display component 5 to give a display of "Different pharmaceutical from last time was detected. Replace?" as shown in FIG. 15f (S308 in FIG. 21).

When the proper pharmaceutical is used, the user presses the setting switch 6c under the "No" display 39 on the display component 5 (S309 in FIG. 21). At this point, the controller 25 clears the pulse count on the encoder 28, after which the motor 13 is rotated forward, the injection operation is executed, and the power is switched off (S309, S310, S311, and S312 in FIG. 21).

In contrast, when the user presses the setting switch 6b under the "Yes" display 40 on the display component 5, the flow moves to S306 in FIG. 21, the motor 13 is reversed, and the cartridge holder 7 is opened up.

Injection Operation

The injection operation in S311 in FIG. 21 will now be described through reference to FIG. 22.

Figure 22:
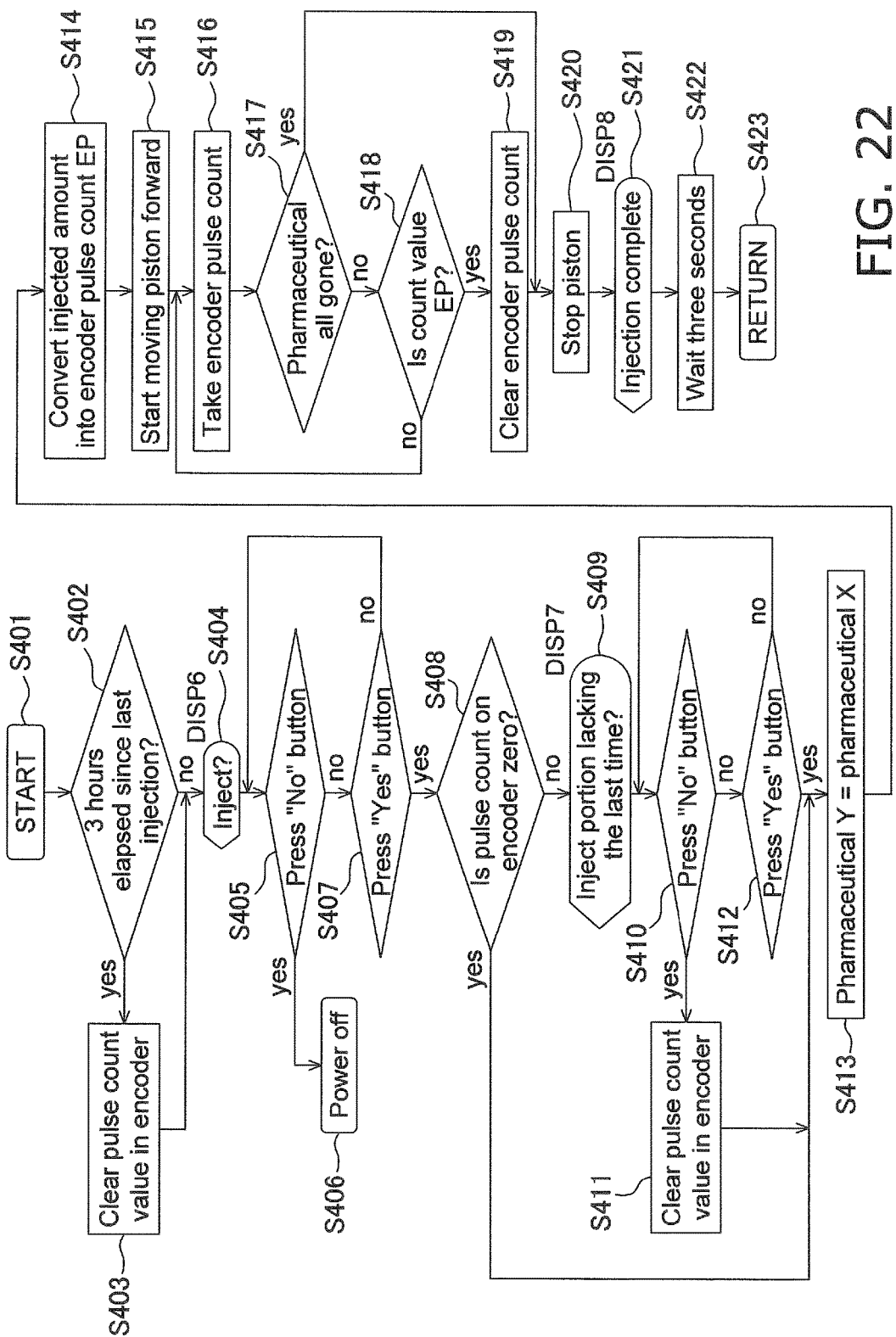
FIG. 22 is an operational flowchart of the pharmaceutical injection device pertaining to an embodiment of the present invention.

The injection operation in S104 and S108 in FIG. 19 is also executed by the operation shown in FIG. 22. When injection operation is executed (S401 in FIG. 22), the controller 25 determines whether or not it has been 3 hours since the last injection, and if 3 or more hours have elapsed, the pulse count is cleared in the encoder 28 (S402 and S403 in FIG. 22).

After this, even if 3 hours have not elapsed in S402 in FIG. 22, the controller 25 causes the display component 5 to give a display of "Inject?" as shown in FIG. 15g (S404 in FIG. 22).

If the user then presses the setting switch 6c under the "No" display 39 shown in FIG. 15g, the power is shut off (S405 and S406 in FIG. 22).

In contrast, if the user presses the setting switch 6b under the "Yes" display 40 shown in FIG. 15g, the controller 25 determines whether or not the pulse counter of the encoder 28 is at zero (S407 and S408 in FIG. 22).

If the value of the encoder 28 is not zero, the controller 25 causes the display component 5 to give a display of "Inject portion lacking the last time?" as shown in FIG. 15h (S409 in FIG. 22).

If the user then presses the setting switch 6c under the "No" display 39 shown in FIG. 15h, the value of the encoder 28 is cleared (S410 and S411 in FIG. 22).

In contrast, if the user presses the setting switch 6b under the "Yes" display 40 shown in FIG. 15h, information about the pharmaceutical to be injected (pharmaceutical X) is stored as the pharmaceutical Y for the next injection, and the amount of pharmaceutical injected is converted into a pulse count (EP) (S412, S413, and S414 in FIG. 22).

The motor 13 is then driven in this state to move the piston 10 forward, and the forward movement at this time is counted by the encoder 28 (S415 and S416 in FIG. 22).

The controller 25 uses this amount of forward movement to confirm whether or not the pharmaceutical cartridge 9 has been emptied of pharmaceutical, and to determine whether or not the count has reached the injection amount (EP) set as the current injection amount. Once this value is reached, the controller 25 clears the count on the encoder 28 and stops the motor 13 (S417, S418, S419, and S420 in FIG. 22).

The display component 5 then gives a display of "Injection complete" as shown in FIG. 15i, and the system waits 3 seconds and then moves to the next state (S421, S422, and S423 in FIG. 22).

That is, in FIG. 21 the control moves to S312 and the power is shut off. S104 in FIG. 19 also moves to S105, and the power is shut off. In S108 in FIG. 19, the control moves to S109.

Other Routines

Other routines in the above series of operations will now be described in order.

In S201 in FIG. 20, if the cartridge holder 7 has not been opened up, the origin sensor 23 detects whether or not the piston 10 has moved all the way to the end.

That is, as discussed above, the origin sensor 23 that senses the origin position of the piston 10 is provided to the rear end side of the piston 10 (the upper end side in FIG. 1), so this origin sensor 23 can detect whether or not the piston 10 has retracted all the way to the end (S211 in FIG. 20). Here, the position at which the protrusion 10a of the piston 10 has approached the origin sensor 23 from the lower part and blocks light serves as the origin position of the piston 10, and the controller 25 uses the pulse count of the motor 13 (via the encoder 28) to detect that the piston 10 has retracted from there to the position specified as the tail end.

If the piston 10 has retracted to the tail end, the controller 25 causes the display component 5 to give a display of "Door won't open. Retry?" as shown in FIG. 15d (S212 in FIG. 20).

Next, if the user presses the setting switch 6c under the "No" display 39, the power is shut off (S213 and S214 in FIG. 20), but if the setting switch 6b under the "Yes" display 40 is pressed, the controller 25 drives the motor 13 to move the piston 10 forward (S215 and S216 in FIG. 20).

When the piston 10 then reaches the retry position for opening the cartridge holder 7, the motor 13 is stopped, after which the motor 13 is reversed to retract the piston 10 (S217, S218, and S219 in FIG. 20). This retry position is the origin position, and the fact that the piston 10 has reached the retry position is detected by the origin sensor 23.

Consequently, if the cartridge holder 7 is opened, the routine proceeds from S201 toward S202 in FIG. 20.

Next, in S301 in FIG. 21, it is determined whether or not the piston 10 has reached the gasket 41, and if it has not reached, the piston 10 is in a state of having advanced further, so the motor 13 is stopped (S314 and S315 in FIG. 21). The stopping of the motor 13 is performed when the controller 25 detects (with the encoder 28) that the position of the piston 10 has reached a preset initial limit position. Here, if a new pharmaceutical cartridge 9 is inserted, manufacturing errors and the like can cause variance in the position of the gasket 41, although it falls within the specified range. Accordingly, the above-mentioned initial limit position is a position at which the gasket 41 has moved too far down, and there is clearly very little pharmaceutical, even when taking into account initial variance in the position of the gasket 41. Whether or not the piston 10 has reached the gasket 41 is determined from a decrease in the rotational speed of the encoder 28 or an increase in the drive current of the motor 13.

That is, at this point no new pharmaceutical cartridge 9 has been installed in the cartridge holder 7, so the controller 25 causes the display component 5 to give a display of "New cartridge not inserted. Insert cartridge" as shown in FIG. 15e (S316 in FIG. 21).

Main Features (1)

The pharmaceutical injection device in this embodiment comprises the main body case 1, the piston 10, the light emitting component 34, the light receiving component 35, and the controller 25. The main body case 1 has the cartridge holder 7 (an example of a holder) in which the pharmaceutical cartridge 9 is housed. The piston 10 pushes the pharmaceutical in the pharmaceutical cartridge 9 housed in the cartridge holder 7 (inside the main body case 1) out of the pharmaceutical cartridge 9. The light emitting component 34 shines light of different colors on the pharmaceutical cartridge 9 disposed in the cartridge holder 7. The light receiving component 35 receives the light that is shined from the light emitting component 34 onto the pharmaceutical cartridge 9 and reflected by the pharmaceutical cartridge 9. The controller 25 successively shines light of different colors from the light emitting component 34 onto the pharmaceutical cartridge 9, and identifies the type of the pharmaceutical cartridge 9 on the basis of the amount of light received by the light receiving component 35 for each color.

As discussed above, the pharmaceutical injection device in this embodiment comprises the light emitting component 34 that shines light of different colors onto the pharmaceutical cartridge 9 disposed in the cartridge holder 7 (an example of a holder), and the light receiving component 35 that receives this light shined from the light emitting component 34 onto the pharmaceutical cartridge 9 and reflected by the pharmaceutical cartridge 9.

The controller 25 successively shines light of different colors from the light emitting component 34 onto the pharmaceutical cartridge 9, and identifies the type of the pharmaceutical cartridge 9 on the basis of the amount of light received by the light receiving component 35 for each color.

Therefore, even if dirt or dust should adhere to the light receiving component 35, when light of different colors is successively shined from the light emitting component 34 onto the pharmaceutical cartridge 9, the amount of light received by the light receiving component for each color will just decrease as the overall sensed level, and in this state, the controller 25 will still be able to properly identify the type of the pharmaceutical cartridge 9 from the amount of light of each color.

More precisely, in the above embodiment, when the dirt determination level Pe is used and an amount of light that is at or above this dirt determination level Pe is obtained, the type of the pharmaceutical cartridge 9 can be properly identified even if the light receiving component 35 is soiled.

Also, when the red LED 341, the green LED 342, and the blue LED 343 are housed as the light emitting component 34 in the same package, and a diffuser plate is disposed in the package, if the dirt adhering to the light emitting component 34 is small, it will not affect color sensing very much, but if the dirt is large, it can be detected by the light receiving component 35. Therefore, even if the light emitting component 34 is soiled, the type of the pharmaceutical cartridge 9 can be properly identified when an amount of light at or above the dirt determination level Pe is obtained.

(2)

With the pharmaceutical injection device in this embodiment, the controller 25 issues a warning output if the amount of light of the sensed color exhibiting the greatest amount of light out of the light quantities for the various colors received by the light receiving component 35 is lower than a specific value.

This makes it possible to detect soiling of the light emitting component 34 or the light receiving component 35, and furthermore a warning to the user can be issued, so it is less likely that the type of pharmaceutical cartridge will be mistakenly identified.

(3)

Also, the pharmaceutical injection device in this embodiment comprises the main body case 1, the piston 10, the red LED 341, the green LED 342, the blue LED 343 (an example of a plurality of light emitting elements), and a photosensor as the light receiving component 35. The main body case 1 has the cartridge holder 7 for holding the pharmaceutical cartridge 9. The piston 10 pushes out the pharmaceutical in the pharmaceutical cartridge 9 housed in the cartridge holder 7 inside the main body case 1. The red LED 341, the green LED 342, and the blue LED 343 shine light of different colors onto the pharmaceutical cartridge 9 disposed in the cartridge holder 7. The light receiving component 35 receives light shined from the red LED 341, the green LED 342, and the blue LED 343 onto the pharmaceutical cartridge 9 and reflected by the pharmaceutical cartridge 9.

Consequently, light of a plurality of colors can be shined onto the pharmaceutical cartridge 9 disposed in the cartridge holder 7, so the type of pharmaceutical cartridge 9 can be properly identified.

Other Embodiments (A)

With the above embodiment, LEDs of three colors were used, namely, the red LED 341, the green LED 342, and the blue LED 343, but if there are few types of pharmaceutical cartridge 9, LEDs of just two different colors may be used.

(B)

Also, rather than using LEDs of three colors, three filters or the like that transmit different wavelengths may be disposed ahead of white light, and light of different colors may be shined on the color label 36 of the pharmaceutical cartridge 9 by successively lighting.

(C)

With the TABLE(0) 42, TABLE(1) 43, and TABLE(2) 44 in the above embodiment, reference data for identifying the pharmaceutical gave only single-point values, such as pharmaceutical (1) (PRG=0, PRB=0.5), but a spread with respect to the value of the reference data may be used in pharmaceutical identification. For instance, it may be determined that pharmaceutical (1) is present when PRG is 0 to 0.2 and PBG is 0.4 to 0.6.

INDUSTRIAL APPLICABILITY

Certain implementations may have the effect of allowing the type of pharmaceutical cartridge to be properly identified, and is useful, for example, as a pharmaceutical injection device for injecting insulin, growth hormone, or other such pharmaceuticals.

The invention claimed is:

1. A pharmaceutical injection device, comprising:
a main body case having a holder for a pharmaceutical cartridge;
a piston configured to push a pharmaceutical of the pharmaceutical cartridge housed in the holder inside the main body case to an outside of the pharmaceutical cartridge;
a light emitting component configured to emit lights of different colors on the pharmaceutical cartridge in the holder;
a light receiving component configured to receive the lights of different colors emitted from the light emitting component onto the pharmaceutical cartridge and reflected by the pharmaceutical cartridge; and
a controller configured to
successively emit the lights of different colors from the light emitting component onto the pharmaceutical cartridge by emitting one of the lights which is of one of the different colors and then emitting another of the lights which is of another of the different colors,
remove a minimum value and a maximum value from an amount of light received by the light receiving component for each of the different colors,
calculate an average value for the amount of light received by the light receiving component for each of the different colors, and
identify a type of pharmaceutical cartridge based on the average value for the amount of light received by the light receiving component for each of the different colors,
wherein the controller is configured to compare the calculated average value for each of the different colors to determine the color having the greatest average value for the amount of light received by the light receiving component and issue a warning output when the calculated average value of the color having the greatest average value is lower than a specific value.

2. The pharmaceutical injection device according to claim 1, further comprising a display component that is connected to the controller, wherein the controller is configured to cause the display component to give a warning display.

3. The pharmaceutical injection device according to claim 2, wherein the warning display is configured to warn of soiling of the holder or the pharmaceutical cartridge.

4. The pharmaceutical injection device according to claim 1, comprising a memory that is connected to the controller, wherein the memory is configured to store reference data for identifying the type of pharmaceutical cartridge from the amount of light received by the light receiving component.

5. The pharmaceutical injection device according to claim 1, wherein the light emitting component has a plurality of LEDs configured to emit the lights of different colors, and the light receiving component has a photosensor.

6. The pharmaceutical injection device according to claim 1, wherein the controller is configured to identify the type of pharmaceutical cartridge based on a ratio of the amount of light of other colors to the amount of light of colors received by the light receiving component whose amount of light is at or above a certain threshold.

7. A method for controlling a pharmaceutical injection device,
the pharmaceutical injection device comprising:
    a main body case having a holder for a pharmaceutical cartridge;
    a piston configured to push a pharmaceutical of the pharmaceutical cartridge housed in the holder inside the main body case to an outside of the pharmaceutical cartridge;
    a light emitting component configured to emit lights of different colors on the pharmaceutical cartridge in the holder; and
    a light receiving component configured to receive the lights emitted from the light emitting component onto the pharmaceutical cartridge and reflected by the pharmaceutical cartridge, and the method comprising:
measuring an amount of light by successively emitting the lights of different colors from the light emitting component onto the pharmaceutical cartridge by emitting one of the lights which is of one of the different colors and then emitting another of the lights which is of another of the different colors, and receiving the lights of different colors reflected from the pharmaceutical cartridge;
removing a minimum value and a maximum value from an amount of the light received by the light receiving component for each of the different colors;
calculating the average value for the amount of light received by the light receiving component for each of the different colors;
identifying a type of pharmaceutical cartridge on based on the average value for the amount of light received by the light receiving component for each of the different colors
comparing the average value for the amount of light received by the light receiving component for each of the different colors; and
issuing a warning output when the average value for the color for which the light receiving component received the greatest average value for the amount of light is lower than a specific value.

* * * * *